US008911755B2

(12) United States Patent
Curry et al.

(10) Patent No.: US 8,911,755 B2
(45) Date of Patent: Dec. 16, 2014

(54) ANTIMICROBIAL COMPOSITION

(75) Inventors: Patrick J. Curry, McGregor, TX (US);
Franklin Irven Diehl, Ruskin, FL (US)

(73) Assignee: EQ Ag Solutions, Hewitt, TX (US)

( * ) Notice: Subject to any disclaimer, the term of this patent is extended or adjusted under 35 U.S.C. 154(b) by 341 days.

(21) Appl. No.: 12/489,362

(22) Filed: Jun. 22, 2009

(65) Prior Publication Data

US 2010/0323037 A1    Dec. 23, 2010

(51) Int. Cl.
| | | |
|---|---|---|
| *A01N 41/10* | (2006.01) | |
| *C11D 3/24* | (2006.01) | |
| *A01N 41/04* | (2006.01) | |
| *C11D 3/04* | (2006.01) | |
| *C11D 3/48* | (2006.01) | |
| *C11D 1/22* | (2006.01) | |
| *C11D 3/34* | (2006.01) | |

(52) U.S. Cl.
CPC ........ *C11D 3/48* (2013.01); *A01N 41/04* (2013.01); *C11D 3/044* (2013.01); *C11D 1/22* (2013.01); *C11D 3/3409* (2013.01)
USPC .......................................... 424/405

(58) Field of Classification Search
None
See application file for complete search history.

(56) References Cited

U.S. PATENT DOCUMENTS

| 4,124,520 | A | | 11/1978 | Schwalley et al. | |
|---|---|---|---|---|---|
| 6,004,604 | A | * | 12/1999 | Thomas et al. | 426/326 |
| 6,617,290 | B2 | * | 9/2003 | Lopes | 510/111 |
| 2004/0043912 | A1 | | 3/2004 | Murch et al. | |
| 2006/0035808 | A1 | * | 2/2006 | Ahmed et al. | 510/499 |
| 2008/0145390 | A1 | | 6/2008 | Taylor et al. | |
| 2009/0192231 | A1 | | 7/2009 | Lemons | |

FOREIGN PATENT DOCUMENTS

| WO | WO-2008031104 | A2 | 3/2008 |
|---|---|---|---|
| WO | WO-2011/005499 | A2 | 1/2011 |
| WO | WO-2011005499 | A3 | 1/2011 |

OTHER PUBLICATIONS

Milne (Gardner's commercially important chemicals; 2005, John Wiley and Sons; pp. 562-563 in part). 2 pages.*
Wash definition [online] retrieved on Dec. 1, 2013 from: http://www.yourdictionary.com/wash; 14 pages.*
International Application Serial No. PCT/US2010/39433, Search Report mailed Dec. 14, 2011, 2 pgs.
International Application Serial No. PCT/US2010/39433, Written Opinion mailed Dec, 14, 2011, 6 pgs.
"Belize Application Serial No. 711.12, Office Action mailed Jun. 29, 2012", 5 pgs.
"Belize Application Serial No. 711.12, Response filed Aug. 16, 2012 to Office Action mailed Jun. 29, 2012", 54 pgs.
"European Application Serial No. 10797559.1, Office Action mailed Nov. 27, 2012", 1 pg.
"European Application Serial No. 10797559.1, Response filed May 28, 2013 to Office Action mailed Nov. 27, 2012", 49 pgs.
"European Application Serial No. 10797559.1, Supplementary Search Report mailed Nov. 9, 2012", 5 pgs.
"International Application Serial No. PCT/US2010/39433, International Preliminary Report on Patentability dated Jan. 4, 2012", 7 pgs.
"Opinion on Trisodium nitrilotriacetate", Plenary Meeting of the Scientific Committee on Consumer Safety, held on Dec. 14, 2010, 34 pgs.
"Colombian Application Serial No. 11-177132, Appeal filed Feb. 7, 2014", 11 pgs.
"Colombian Application Serial No. 11-177132, Office Action mailed Jan. 17, 2014", (w/ English Translation), 15 pgs.
"Colombian Application Serial No. 11-177132, Office Action mailed Jul. 30, 2013", (w/ English Translation), 17 pgs.
"Colombian Application Serial No. 11-177132, Response filed Oct. 24, 2013 to Office Action mailed Jul. 30, 2013", 26 pgs.
"European Application Serial No. 10797559.1, Examination Notification Art. 94(3) mailed Nov. 27, 2013", 4 pgs.

* cited by examiner

*Primary Examiner* — Ernst V Arnold
(74) *Attorney, Agent, or Firm* — Schwegman Lundberg & Woessner, P.A.

(57) ABSTRACT

A composition that includes ethylhexyl sulfate or a salt thereof, an alkylbenzenesulfonic acid or a salt thereof, and a carrier. The ethylhexyl sulfate, or salt thereof, and the alkylbenzenesulfonic acid, or salt thereof, are present in a weight ratio of at least about 1:2. The composition can be used for killing or inhibiting a microorganism or pathogen (e.g., bacteria, gram-negative bacteria, gram-positive bacteria, enteric bacteria, virus, fungus, mold, mildew or powdery mildew).

28 Claims, No Drawings

ANTIMICROBIAL COMPOSITION

BACKGROUND

Contaminants, such as dirt, fertilizer, fungicide, pesticide, feces, mold, insect, bacteria and microbial pathogens can be the cause of disagreeable taste in raw fruits and vegetables and often cause illness and sometimes fatalities. Therefore, the prevention or elimination of contamination of food products by pathogenic microorganisms is important to protect public health. Recent fatal outbreaks of Escherichia coli infection following ingestion of infected food (e.g., peanut butter) have publicized the severity of this public health problem. Many pathogenic microorganisms can be transmitted to food, such as fresh produce, during harvesting, preparation or handling. Moreover, fruits and vegetables are often handled by numerous people (from agricultural workers to consumers) in food distribution channels, which provides multiple opportunities for infection of the food with pathogens. Thus, microorganisms can accumulate at a variety of different points in a food manufacturing operation; the more points at which viable microorganisms can be controlled, the lower the chances of food contamination and the safer the manufacturing process.

Scientists and public health officials have sought to reduce the incidence of human infections from pathogenic bacteria such as *Salmonella* and *Escherichia coli* ("*E. coli*"). Food products are a significant source of human infection by pathogens. Animal food products can become contaminated with bacterial food-borne pathogens as a result of exposure of the animal carcass to fecal matter. Likewise, fruits and vegetables can become contaminated by contact with pathogenic bacteria. The pathogens are then transmitted to humans during consumption of the contaminated food.

Antimicrobial agents have been used over the years to control or inhibit the growth of various microorganisms in various products and particularly food compositions. The increased use of antimicrobial agents has resulted in numerous pathogenic microorganisms developing new strains that are resistant to many of the commonly used antibacterial agents.

Thus, what is needed are compositions/antibacterial agents and methods that effectively inhibit, inactivate, kill or remove various pathogens (e.g., *Salmonella*) that cause foodborne infections (e.g., salmonellosis) from surfaces during food manufacturing processes. These pathogenic microorganisms can be present, e.g., on a topical surface of a human, on a surface of equipment used in the food industry, a food preparation surface (e.g., a cooking surface) or a food storage surface. Alternatively, the pathogenic microorganism can be present, e.g., on the surface of a food product (e.g., fruit or vegetable), either pre-harvest or post-harvest.

SUMMARY

The compositions described herein are effective in killing or diminishing a variety of organisms, such as bacteria, mold, yeast, fungus and/or virus. For example, in one embodiment the compositions described herein kill 99.9% of harmful bacteria including *Salmonella typhimurium* and *Staphylococcus aureus*. Additionally, the compositions described herein rapidly (e.g., in 30 seconds or less) kill bacteria or otherwise reduce the bacteria count on, for example, surfaces, including surfaces of raw fruits and vegetables or food preparation surfaces (e.g., countertops, bowls, utensils) and surfaces of animals, such as human hands.

The presently disclosed subject matter includes a composition that includes ethylhexyl sulfate or a salt thereof; an alkylbenzenesulfonic acid or a salt thereof; and a carrier. The ethylhexyl sulfate, or salt thereof; and the alkylbenzenesulfonic acid, or salt thereof, are present in a weight ratio of at least about 1:2.

In a specific embodiment, the composition includes: (a) at least about 4 wt.% ethylhexyl sulfate, or salt thereof; (b) at least about 6 wt.% dodecylbenzenesulfonic acid, or salt thereof; (c) at least about 0.5 wt.% sodium hydroxide, and (d) the balance of water.

The composition can be in the form of a cream, gel, paste, ointment, lotion, fluid liquid, liquid soap, or aerosol spray. Alternatively, the composition can be physically present in a wipe. The wipe can include a flexible cloth, wherein the composition is positioned (i.e., located) on at least a portion of a surface of the flexible cloth.

The composition, e.g., in the form of a cream, gel, paste, ointment, lotion, fluid liquid, liquid soap, aerosol spray, or physically present in a wipe, can be used for antiseptic cleansing of a topical surface of a human. Additionally, the composition can be used for antiseptic cleansing of a surface of equipment used in the food industry. Additionally, the composition can be used as a hand sanitizer. Additionally, the composition can be used as a residential sanitizer, commercial sanitizer and industrial sanitizer.

The presently disclosed subject matter provides for a method of killing or inhibiting a microorganism or pathogen. The method includes contacting the microorganism or pathogen with an effective amount of the composition described herein, for a period of time effective to kill or inhibit the microorganism or pathogen. The microorganism or pathogen can be a bacteria, gram-negative bacteria, gram-positive bacteria, enteric bacteria, virus, fungus, mold, mildew or powdery mildew.

The presently disclosed subject matter also provides for a method of washing a plant. The method includes contacting the plant with an effective amount of the composition described herein, for a period of time effective to wash the plant. An edible part of the plant can be washed. Additionally, the plant can be washed before harvesting. Alternatively, the plant can be washed after harvesting.

The presently disclosed subject matter also provides for a method of sanitizing a plant. The method includes contacting the plant with an effective amount of the composition described herein, for a period of time effective to sanitize the plant. An edible part of the plant can be sanitized. Additionally, the plant can be sanitized before harvesting. Alternatively, the plant can be sanitized after harvesting.

The presently disclosed subject matter also provides for a method of washing (cleaning) a surface of equipment used in the food industry. The method includes contacting the surface with an effective amount of the composition described herein, for a period of time effective to wash the surface.

The presently disclosed subject matter also provides for a method of sanitizing a surface of equipment used in the food industry. The method includes contacting the surface with an effective amount of the composition described herein, for a period of time effective to sanitize the surface.

The presently disclosed subject matter also provides for a method of cleaning (washing) a food preparation surface, such as a cooking surface, or a food storage surface. The method includes contacting the surface with an effective amount of the composition described herein, for a period of time effective to clean the surface.

The presently disclosed subject matter also provides for a method of sanitizing a food preparation surface, such as a cooking surface, or a food storage surface. The method includes contacting the surface with an effective amount of the composition described herein, for a period of time effective to sanitize the surface.

DETAILED DESCRIPTION

The compositions described herein are effective against a variety of organisms, such as bacteria, mold, yeast, fungus and/or virus. For example, in one embodiment the compositions described herein kill 99.9% of harmful bacteria including *Salmonella typhimurium* and *Staphylococcus aureus*. Additionally, the compositions described herein rapidly (e.g., in 30 seconds or less) kill bacteria or otherwise reduce the bacteria count on, for example, surfaces, including surfaces of raw fruits and vegetables and surfaces of animals, such as human hands.

The presently disclosed subject matter includes a composition that includes ethylhexyl sulfate or a salt thereof, an alkylbenzenesulfonic acid or a salt thereof, and a carrier. The ethylhexyl sulfate, or salt thereof, and the alkylbenzenesulfonic acid, or salt thereof, are present in a weight ratio of at least about 1:2. That is, based upon a weight basis, the amount of ethylhexyl sulfate, or salt thereof is at least about a half (i.e., 50%) that of the alkylbenzenesulfonic acid, or salt thereof.

In a specific embodiment, the ethylhexyl sulfate, or salt thereof, and the alkylbenzenesulfonic acid, or salt thereof, are present in a weight ratio of least about 1:1. That is, based upon a weight basis, the amount of ethylhexyl sulfate, or salt thereof is at least about equal (i.e., 100%) that of the alkylbenzenesulfonic acid, or salt thereof.

In a more specific embodiment, the ethylhexyl sulfate, or salt thereof, and the alkylbenzenesulfonic acid, or salt thereof, are present in a weight ratio of about 1:2 to about 3:1. That is, based upon a weight basis, the amount of ethylhexyl sulfate, or salt thereof is at least a half (i.e., 50%) that of the alkylbenzenesulfonic acid, or salt thereof; and is no more than about three times (i.e., 300%) that of the alkylbenzenesulfonic acid, or salt thereof.

In a more specific embodiment, the ethylhexyl sulfate, or salt thereof, and the alkylbenzenesulfonic acid, or salt thereof, are present in a weight ratio of about 1:2 to about 2:1. That is, based upon a weight basis, the amount of ethylhexyl sulfate, or salt thereof is at least about a half (i.e., 50%) that of the alkylbenzenesulfonic acid, or salt thereof; and is no more than about two times (i.e., 200%) that of the alkylbenzenesulfonic acid, or salt thereof.

In a more specific embodiment, the ethylhexyl sulfate, or salt thereof, and the alkylbenzenesulfonic acid, or salt thereof, are present in a weight ratio of about 1:2 to about 1.5:1. That is, based upon a weight basis, the amount of ethylhexyl sulfate, or salt thereof is at least about a half (i.e., 50%) that of the alkylbenzenesulfonic acid, or salt thereof; and is no more than about one and a half times (i.e., 150%) that of the alkylbenzenesulfonic acid, or salt thereof.

Ethylhexyl sulfate refers to a compound of the formula

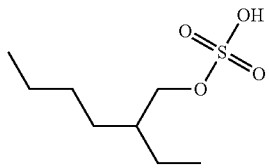

Sodium ethylhexyl sulfate, CAS Reg. No. 126-92-1, alternatively known as NAS 08 or NIAPROOF 08, is present in NIAPROOF anionic surfactant 08 in 38.5-40 wt. %. NIAPROOI- anionic surfactant 08 also includes sodium chloride (1.5-2.5 wt. %) and the balance of water. NIAPROOF anionic surfactant 08 is commercially available from Niacet Corp. (Niagara Falls, N.Y.).

An alkylbenzenesulfonic acid refers to a compound of the formula

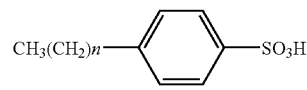

wherein n is about 5 to about 20. In specific embodiments, n will have an average value of 5, 6, 7, 8, 9, 10, 11, 12, 13, 14, 15, 16, 17, 18, 19 or 20. In further specific embodiments, n will have an average value of about 8 to about 12. In further specific embodiments, n will have an average value of about 9 to about 11. Alkylbenzenesulfonic acid ($C_{10}$-$C_{16}$), CAS Reg. No. 68584-22-5, is present in Bio-Soft S-101 in over 95.5%. Benzene and other aromatic derivatives, are also present in Bio-Soft S-101 in 2%. Additionally, sulfuric acid (1.3%) is present in Bio-Soft S-101. Bio-Soft S-101 is commercially available from Stepan Co. (Northfield, Ill.).

Carrier

The composition includes a carrier. A carrier refers to a substance in which the ethylhexyl sulfate, or salt thereof, and the alkylbenzenesulfonic acid, or salt thereof, can be dissolved into or mixed with. Any suitable and effective carrier can be employed, provided the carrier is stable over the periods of time typically encountered with the manufacturing, shipping and storage of the composition. Additionally, the carrier will preferably be chemically and physically compatible with the ethylhexyl sulfate, or salt thereof, and the alkylbenzenesulfonic acid, or salt thereof.

In a specific embodiment, the carrier includes at least one of water, ethanol, triethylene glycol, ethylene glycol, glycerin, propylene glycol, triacetin, 1,3-propane diol, 2-methyl-1,3-propane diol, glycerol ricinoleate, PEG-6 caprylic/capric glycerides, caprylic/capric triglycerides, propyleneglycol dicaprylate/dicaprate, glycerol monostearate, glycerol monocaprylate, glycerol monolaurate, neopentyl alcohol, 1-hexademayol, hydroxypropyl beta-cyclodextrin, vitamin E, vitamin E acetate, deoxycholic acid, taurodeoxycholic acid, 3-[(3-cholamidopropyl)dimethylammonio]-1-propane-sulfonate, BigCHAP, cholic acid, cholesterol NF, propylene carbonate, lecithin, and salts thereof. In a more specific embodiment, the carrier includes water.

Base

In specific embodiments, the composition can optionally further include a base. The base can be an organic base or an inorganic base. The base, when present in the composition, will effectively produce one or more hydroxyl ions ($OH^-$). In a specific embodiment, the base can include at least one of a lithium ion ($Li^+$), a sodium ion ($Na^+$), a potassium ion ($K^+$), a calcium ion ($Ca^{2+}$), and a barium ion ($Ba^+$). More specifically, the base can include at least one of sodium hydroxide (NaOH) and potassium hydroxide (KOH).

The base can be present in any suitable and appropriate amount. For example, the base can be present in an amount, such that the pH of the composition is above about 6. Specifically, the base can be present in an amount, such that the pH of the composition is, e.g., about 6 to about 13. More specifically, the base can be present in an amount, such that the pH of the composition is, e.g., about 7 to about 9, or about 7 to about 8.5. Additionally, the base can be employed, e.g., not to adjust the pH above 7 (i.e., neutral pH), but to neutralize, or partially neutralize, acid present in the composition. For example, the base can be employed to neutralize, or partially neutralize the sulfuric acid present from the Bio-Soft S-101.

The amount of base can depend, e.g., upon the amount of ethylhexyl sulfate, or salt thereof, and the alkylbenzenesulfonic acid, or salt thereof. For example, the base (e.g., sodium hydroxide, potassium hydroxide, or combination thereof) can be present in a weight ratio of less than about 1:4, relative to the ethylhexyl sulfate, or suitable salt thereof.

Sodium Chloride

The commercial product NIAPROOF 08 currently includes sodium chloride (1.5-2.5 wt. %). As such, when the current formulation of NIAPROOF 08 is employed as the source of the ethylhexyl sulfate, or salt thereof, sodium chloride will be present in the composition. Alternatively, when the current formulation of NIAPROOF 08 is not employed as the source of the ethylhexyl sulfate, or salt thereof, sodium chloride can be included within the composition, or the sodium chloride can be omitted from the composition.

When present, the sodium chloride can be present in up to about 5 wt. % of the composition, up to about 1 wt. % of the composition or up to about 0.1 wt. % of the composition.

Acid

The commercial product Bio-Soft S-101 currently includes sulfuric acid (1.3%). As such, when the current formulation of Bio-Soft S-101 is employed as the source of the alkylbenzenesulfonic acid, or salt thereof, sulfuric acid will be present in the composition. The sulfuric acid can be present in the free acid form, or can be used to neutralize any base present in the composition. Alternatively, when the current formulation of Bio-Soft S-101 is not employed as the source of the alkylbenzenesulfonic acid, or salt thereof, sulfuric acid can be included within the composition, or the sulfuric acid can be omitted from the composition. Likewise, other suitable acids (e.g., lactic acid) can be employed in the composition.

When present, each of the acids can independently be present in up to about 5 wt. % of the composition, up to about 1 wt. % of the composition or up to about 0.1 wt. % of the composition.

Disinfectant

The composition can optionally further include a disinfectant. Additionally, the methods described herein can further include the use of a disinfectant, in combination with the composition described herein. In such a situation, the use of the disinfectant can be concurrent with the use of the composition, or can be sequential with the use of the composition.

The disinfectant can be any substance that effectively inhibits or kills a microorganism. Specific disinfectants include, e.g., chlorine dioxide, chlorine gas, or any substance that would effectively generate chlorine gas, e.g., upon contact with the composition described herein. Additional specific disinfectants include e.g., ozone ($O_3$), lactic acid, ultraviolet light, peroxides, peracetic acid (peroxyacetic acid, or PAA), potassium sorbate and lactic acid.

Formulation

The composition can be formulated into any suitable and effective formulation.

Specific formulations include, e.g., creams, gels, pastes, ointments, lotions, fluid liquids liquid soaps, and aerosol sprays.

Alternatively, the composition can be physically present in a wipe. The wipe can include a flexible cloth, wherein the composition is positioned (i.e., located) on at least a portion of a surface of the flexible cloth. The flexible cloth can be manufactured from any suitable and effective materials. For example, the flexible cloth can include a non-woven fabric. Specifically, the flexible cloth can include at least one of polycellulose fibers, polyester fibers, polyurethane fibers, polyolefin fibers, polyamide fibers, cotton fibers, copolyester fibers and films. Additionally, the composition can be at least partially embedded in at least a portion of the flexible cloth.

Antibiotic Agent

The composition can optionally further include an antibiotic agent. Suitable specific antibiotic agents include, e.g., cilastatin, clavulanic acid, folinic acid, probenecid, pyridoxine, sulbactam, dapsone, ethambutol, isoniazid, pyrazinamide, rifampin, streptomycin, capreomycin, ethionamide, para aminosalicylic acid, cycloserine, ciprofloxacin, nalidixic acid, norfloxacin, ofloxacin, imipenem, meropenem, cilastatin, cefadroxil, cefazolin, cephalexin, cephalothin, cefaclor, cefamandole, cefonicid, cefoxitin, cefuroxime, cefoperazone, cefotaxime, ceftazidime, ceftazidime, ceftizoxime, ceftriaxone, moxalactam, cefepime, bacitracin, vancomycin, aztreonam, amoxicillin, clavulanic acid, benzathine, penicillin g, penicillin v, ampicillin, carbenicillin indanyl, carbenicillin, mezlocillin, piperacillin, ticarcillin, cloxacillin, dicloxacillin, floxacillin, methicillin, nafcillin, oxacillin, colistimethate, polymyxin b, trimethoprim, co-trimoxazole, mafenide, sulfadiazine, sodium sulfacetamide, sulfacytine, sulfadiazine, sulfamethoxazole, sulfapyridine, sulfasalazine, sulfisoxazole, chloramphenicol, clindamycin, spectinomycin, azithromycin, clarithromycin, erythromycin, erythromycin estolate, spiramycin, chlortetracycline, demeclocycline, doxycycline, minocycline, oxytetracycline, amikacin, kanamycin, neomycin, streptomycin, tobramycin, nitrofurantoin, griseofulvin, potassium iodide, fluconazole, itraconazole, ketoconazole, miconazole, clotrimazole, amphotericin b, nystatin, niclosamide, nifurtimox, piperazine, praziquantel, pyrantel pamoate, thiabendazole, amodiaquine, chloroquine, hydroxychloroquine, mefloquine, primaquine, pyrimethamine, quinidine gluconate, fansidar, diloxanide furoate, melarsoprol, nifurtimox, paromomycin, pentamidine, sodium stibogluconate, suramin, metronidazole, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, foscarnet, 3-deoxythmidin-2-ene, dideoxycytosine, dideoxyinosine, lamivudine, azidothymidine, indinavir, ritonavir, saquinavir, acyclovir, idoxuridine, ribavirin, vidarabine, amantidine, rinantidine, and salts thereof.

The antibiotic agent can be present in the composition in any suitable and effective amount, provided the antibiotic agent affectively inhibits or kills the desired bacterium. Specific exemplary amounts include, e.g., up to about 10 wt. % of the composition, up to about 5.wt. % of the composition, or up to about 1 wt. % of the composition.

Antiviral Agent

The composition can optionally further include an antiviral agent. Suitable specific antiviral agents include, e.g.,*Echinacea* (*Echinacea angustifolia, E. pallida, E. Purpurea*), Elderberry (*Sambucus nigra*), Garlic (*Allium sativum*), Lemon balm (*Glycyrrhiza Glabra*), Astragalus (*Astragalus membranaceus*), eyebright (*Euphrasia officinalis*), sage (*salvia Officinalis*), yarrow (*Achillea millefolium*), nettles (*Urtica dioica*), peppermint (*Menthe piperiya*), Ephedra (*Ephedra sinica*), marshmallow root (*Althea officinalis*), mullein leaves or flowers (*Verbascum* spp.), plantain leaf (*Plantago lanceolata, P. major*), licorice root, thyme (*Thymus vulgaris*), boneset (*Eupatorium perfoliatum*), feverfew (*Tanacetum parthenium*), catnip (*Nepeta cataria*), yarrow (*Achillea millefolium*), elder flower (*Sambucus nigra, S. mayadenis*), ginger (*Zingiber officinale*), Ginkgo biloba, St. John's wort (*Hypericum perforatum* L.), zinc, lysine, foscarnet, 3-deoxythymidine-2-ene, dideoxycytosine, dideoxyinosine, lamivudine, azidothymidine, indinavir, ritonavir, saquinavir, acyclovir, idoxuridine, ribavirin, vidarabine, amantadine, ranitidine, viracea, cytovene, famciclovir, valaciclovir, penciclovir, hexadecyloxypropyl-cidofovir (HDP-CDV), nonoxynol-9, docosanol (n-docosanol, 1-docosanol, or behenyl alcohol; which is a saturated 22-carbon straight-chain alcohol), triacontanol, and salts thereof.

The antiviral agent can be present in the composition in any suitable and effective amount, provided the antiviral agent affectively inhibits or kills the desired virus. Specific exemplary amounts include, e.g., up to about 10 wt. % of the composition, up to about 5 wt. % of the composition, or up to about 1 wt. % of the composition.

Antimicrobial Agent or Preservative

The composition can optionally further include an antimicrobial agent or preservative. Suitable specific antimicrobial agents or preservatives include, e.g., quat-15, a paraben, dichlorobenzyl alcohol, ethylene diamine tetraacetic acid, formaldehyde, gum benzoin, imidazolidinyl urea, phenylmercuric acetate, poly aminopropyl biguanide, proply gallate, sorbic acid, cresol, chloroacetamide sodium benzoate, chloromethyl-methylisothiazolinone, chloromethyl-methylisothiazolon, chloromethyl-methylisothiazolinone benzalkonium chloride, an octylisothiazolinone benzimidazol-compound, chloromethyl-methylisothiazolinone octylisothiazolinone, o-phenylphenol benzisothiazolinone, o-phenylphenol benzisothiazolinone, benzisothiazolinone, an aliphatic amine of 2-thiopyridineoxide, benzoic acid, editic acid, phenolic acid, benzyl alcohol, isopropyl alcohol, benzethonium chloride, bronopol, cetrimide, chlorohexidine, chlorobutanol, chlorocresol, phenol, phenoxyethanol, phenyl ethyl alcohol, phenylmercuric acetate, phenylmercuric borate, phenylmercuric nitrate, potassium sorbate, propylene glycol, sodium benzoate, sodium propionate, thimerosal, and salts thereof.

The antimicrobial agent or preservative can be present in the composition in any suitable and effective amount, provided the antimicrobial agent or preservative affectively inhibits or kills the microorganism. Specific exemplary amounts include, e.g., up to about 10 wt. % of the composition, up to about 5 wt. % of the composition, or up to about 1 wt. % of the composition.

Skin Protectant

The composition can optionally further include a skin protectant. The skin protectant can act as a topical humectant, a topical conditioner, or combination thereof. Suitable specific skin protectants include, e.g., aloe, lanolin, glycerin, calamine, Vitamin E, Vitamin E acetate, Vitamin C, allantoin, aluminum hydroxide gel, bismuth subnitrate, boric acid, calamine, cocoa butter, dimethicone, kaolin, live yeast cell derivative, petrolatum, pyridoxine hydrochloride, shark liver oil, sodium bicarbonate, sulfur, tannic acid, topical starch, trolamine, white petrolatum, zinc acetate, zinc carbonate zinc oxide, zinc sulfate, and shea butter.

The skin protectant can be present in the composition in any suitable and effective amount, provided the skin protectant imparts the desired conditioning and/or moisturizing effect. Specific exemplary amounts include, e.g., up to about 10 wt. % of the composition, up to about 5 wt. % of the composition, or up to about 1 wt. % of the composition.

In various embodiments, the composition described herein can further optionally include one or more of a gelling agent (e.g., a synthetic polymer of acrylic acid), an antiseptic (e.g., at least one of a ($C_1$-$C_{12}$)alkyl, substituted with one or more hydroxyl groups such as ethyl alcohol, isopropanol, erythritol, ethylene glycol, propylene glycol, triethylene glycol, tetraethylene glycol, and/or sorbitol), a fragrance, a coloring agent, and an essential oil.

In various embodiments, the composition described herein can effectively kill or inhibit a microorganism or pathogen, wherein the microorganism or pathogen is contacted with an effective amount of the composition, for a period of time effective to kill or inhibit the microorganism or pathogen. In specific embodiments, the contacting can occur on the surface of a plant or a mammal, or can occur on a residential, commercial or industrial surface, such as a food preparation surface (e.g., a cooking surface) or a food storage surface.

Plant

As used herein, "plant" or "plant tissue" refers to the tissue of any organism of the plant kingdom, as opposed to one of the animal kingdom or of the kingdoms of Fungi, Protista, or Monera. The plant tissue can be any portion or portions of the plant (e.g., bark, roots, leaves, flowers, needles, bulbs, berries, rhizomes, rootstocks, stems, and seeds), as well as the entire plant. The tissues of a plant ("plant tissue") generally fall into three main categories: dermal tissue, ground tissue, and vascular tissue. Dermal tissue refers to the "skin" layer of all plant organs and is responsible for environmental interaction (light passage, gas exchange, pathogen recognition and protection, color display, etc.). Dermal tissue is composed of epidermal cells, closely packed cells that secrete a waxy cuticle that aids in the prevention of water loss. Ground tissue lies between dermal tissue and vascular tissue. The ground tissue comprises the bulk of the primary plant body. Parenchyma, collenchyma, and sclerenchyma cells are common in the ground tissue. In roots, the ground tissue may store sugars or starches to fuel the spring sap flow; in leaves, the ground tissue is the layer responsible for photosynthesis (the mesophyll). Vascular tissue transports food, water, hormones and minerals within the plant. Vascular tissue includes xylem, phloem, parenchyma, and cambium cells.

As used herein, "bark" refers to the dry, dead outer covering of woody branches, stems and roots of plants that is very distinct and separable from the wood itself. It includes all tissue outside the cambium (growth layer between bark and wood).

As used here the terms "leaf" or "leaves" refer to those parts of a plant which grow along the sides of branches or stems or at the bases of plants. Most are green and contain chlorophyll, though they vary in their shapes and sizes. Leaves are the part of the plant that ordinarily performs photosynthesis (the process that converts sunlight and carbon dioxide into energy).

As used herein, "needle" generally refers to a narrow stiff leaf, such as those of conifers (e.g., pine trees).

As used herein, "root" refers to the part of a plant, normally underground, that absorbs nutrients and anchors the plant into the ground.

As used herein, "bulb" refers to a spheroidal body growing from a plant either above or below the ground (usually below), which is usually a bud, consisting of a cluster of partially developed leaves, and producing, as it grows, a stem above, and roots below, (e.g., the onion or tulip bulb). A true bulb is a complete package containing next year's plant (flower) already forming inside. The contents of the bulb are often enclosed in protective, fleshy scales, which are held together by a small basal plate. The scales are modified leaves that contain enough nutrients to sustain the plant through dormancy and early growth. They may be loose and open like those of a lily, or tightly closed like those of a hyacinth. In many bulbs, a paper-thin tunic protects the scales (lilies don't have a tunic). Roots will grow from the bulb's basal plate.

As used herein, "berry" refers to any small fruit that is pulpy or succulent throughout, having seeds loosely imbedded in the pulp, such as the currant, grape, or blueberry. Berry can be further defined as an indehiscent fruit derived from a single ovary and having the whole wall fleshy, such as the grape or tomato. Furthermore, berries come in various structures including simple, such grape; blueberry, cranberry, or aggregate, such as blackberry; raspberry, strawberry or mulberry.

As used herein, "rhizome" refers to a horizontal, usually underground stem that often sends out roots and shoots from its nodes (also called rootstalk or rootstock).

As used herein, "rootstock" refers to a robust plant that provides the root system in grafting, also known as a stock. Scions and buds are grafted and budded to a rootstock or stock. Rootstock also refers to the elongated and often thick rhizomes of certain perennial herbaceous plants such as the Iris, Aspidistra and Solomon's Seal.

As used herein, "stem" refers to the main (usually aerial) axis (sometimes referred to as the trunk or stalk) of a tree, shrub, or plant. "Stem" also refers to the part of the plant that supports the leaves, flowers or fruits of a plant, such as the peduncle of a fruit or the pedicel of a flower.

As used herein, "seed" refers to a ripened ovule, consisting of an embryo with one or more integuments, or coverings, such as an apple seed, a currant seed, dill seed, or kola nut seed. By germination, most seeds produces a new plant. "Seed" also refers to any small seedlike fruit, though it may consist of a pericarp, or even a calyx, as well as the seed proper, such as a parsnip seed or thistle seed. The seed proper has an outer and an inner coat, and within these the kernel or nucleus. The kernel is either the embryo alone, or the embryo enclosed in the albumen, which is the material for the nourishment of the developing embryo. The scar on a seed, left where the stem parted from it, is called the hilum, and the closed orifice of the ovule, the micropyle.

In a specific embodiment, the plant or plant tissue includes a fruit. In a more specific embodiment, the plant or plant tissue includes a true berry (e.g., blackcurrant, redcurrant, gooseberry, tomato, eggplant, guava, lucuma, chili pepper, pomegranate, kiwifruit, or grape); a pepo (e.g., pumpkin, gourd, cucumber or melon); a hesperidium (e.g., orange, lemon, lime or grapefruit); a false berry or epigynous (e.g., banana, cranberry or blueberry); an aggregate fruit (e.g., blackberry, raspberry, boysenberry or hedge apple); a multiple fruit (e.g., pineapple, fig, or mulberry); or another accessory fruit (e.g., apple, apricot, peach, cherry, green bean, sunflower seed, strawberry or plum).

In a specific embodiment, the plant or plant tissue includes an edible part of the plant. The term "vegetable" generally refers to the edible parts of plants. The term "vegetable" therefore includes, e.g., mushrooms which belong to the biological kingdom Fungi, not the plant kingdom; as well as nuts, seeds, grains, herbs, spices and culinary fruits.

In a more specific embodiment, the plant or plant tissue includes a leafy and salad vegetable, a fruiting and flowering vegetable, a podded vegetable, a bulb and stem vegetable, a root and tuberous vegetable or a sea vegetable. Suitable exemplary leafy and salad vegetables, fruiting and flowering vegetables, podded vegetables, bulb and stem vegetables, and root and tuberous vegetables are shown in Table I below.

TABLE I

| Leafy and salad vegetables | Fruiting and flowering vegetables | Podded vegetables | Bulb and stem vegetables | Root and tuberous vegetables |
|---|---|---|---|---|
| Amaranth (*Amaranthus cruentus*) | Breadfruit (*Artocarpus altilis*) | American groundnut (*Apios americana*) | Asparagus (*Asparagus officinalis*) | Ahipa (*Pachyrhizus ahipa*) |
| Beet greens (*Beta vulgaris* subsp. *vulgaris*) | Acorn squash (*Cucurbita pepo*) | Azuki bean (*Vigna angularis*) | Cardoon (*Cynara cardunculus*) | Arracacha (*Arracacia xanthorrhiza*)) |
| Broccoli Rabe (*Brassica rapa* subsp. *rapa*) | Armenian cucumber (*Cucumis melo* Flexuosus group) | Black-eyed pea (*Vigna unguiculata* subsp. *unguiculata*) | Celeriac (*Apium graveolens* var. *rapaceum*) | Bamboo shoot |
| Bitterleaf (*Vernonia calvana*) | Eggplant or Aubergine (*Solanum melongena*) | Chickpea (*Cicer arietinum*) | Celery (*Apium graveolens*) | Beetroot (*Beta vulgaris* subsp. *vulgaris*) |
| Bok choy (*Brassica rapa* Chinensis group) | Bell pepper (*Capsicum annuum*) | Drumstick (*Moringa oleifera*) | Elephant Garlic (*Allium ampeloprasum* var. *ampeloprasum*) | Black cumin (*Bunium persicum*) |
| Brussels sprout (*Brassica oleracea* Gemmifera group) | Bitter melon (*Momordica charantia*) | Dolichos bean (*Lablab purpureus*) | Florence fennel (*Foeniculum vulgare* var. dulce) | Burdock (*Arctium*) |
| Cabbage (*Brassica oleracea* Capitata group) | Caigua (*Cyclanthera pedata*) | Fava bean (*Vicia faba*) | Garlic (*Allium sativum*) | Broadleaf arrowhead (*Sagittaria latifolia*) |
| Catsear (*Hypochaeris radicata*) | Cape Gooseberry (*Physalis peruviana*) | French bean (*Phaseolus vulgaris*) | Kohlrabi (*Brassica oleracea* Gongylodes group) | Camas (*Camassia*) |
| Celtuce (*Lactuca sativa* var. *asparagina*) | Cayenne pepper (*Capsicum frutescens*) | Guar (*Cyamopsis tetragonoloba*) | Kurrat (*Allium ampeloprasum* var. *kurrat*) | Canna (*Canna* spp.) |
| Ceylon spinach (*Basella alba*) | Chayote (*Sechium edule*) | Horse gram (*Macrotyloma uniflorum*) | Leek (*Allium porrum*) | Carrot (*Daucus carota*) |
| Chicory (*Cichorium intybus*) | Chili pepper (*Capsicum annuum* Longum group) | Indian pea (*Lathyrus sativus*) | Lotus root (*Nelumbo nucifera*) | Cassava (*Manihot esculenta*) |
| Chinese Mallow (*Malva verticillata*) | Cucumber (*Cucumis sativus*) | Lentil (*Lens culinaris*) | Nopal (*Opuntia ficus-indica*) | Chinese artichoke (*Stachys affinis*) |
| Chrysanthemum leaves (*Chrysanthemum coronarium*) | Luffa (*Luffa acutangula*, *Luffa aegyptiaca*) | Moth bean (*Vigna acontifolia*) | Onion (*Allium cepa*) | Daikon (*Raphanus sativus* Longipinnatus group) |
| Corn salad (*Valerianella locusta*) | Malabar gourd (*Cucurbita ficifolia*) | Mung bean (*Vigna radiata*) | Prussian asparagus (*Ornithogalum pyrenaicum*) | Earthnut pea (*Lathyrus tuberosus*) |
| Cress (*Lepidium sativum*) green beans | Parwal (*Trichosanthes dioica*) *Lycopersicon* | Okra (*Abelmoschus esculentus*) | Shallot (*Allium cepa* Aggregatum group) | Elephant Foot yam *Amorphophallus_paeoniifolius*) |
|  |  | Pea (*Pisum sativum*) |  | Ensete (*Ensete ventricosum*) |
|  |  | Peanut (*Arachis hypogaea*) |  | Ginger (*Zingiber officinale*) |
|  |  | Pigeon pea (*Cajanus cajan*) |  | Gobo (*Arctium lappa*) |
|  |  |  |  | Hamburg parsley (*Petroselinum crispum* var. *tuberosum*) |
|  |  |  |  | Jerusalem artichoke (*Helianthus tuberosus*) |
|  |  |  |  | Jicama (*Pachyrhizus erosus*) |
|  |  |  |  | Parsnip (*Pastinaca sativa*) |
|  |  |  |  | Pignut (*Conopodium majus*) |
|  |  |  |  | Plectranthus (*Plectranthus* spp.) |
|  |  |  |  | Potato (*Solanum tuberosum*) |

TABLE I-continued

| Leafy and salad vegetables | Fruiting and flowering vegetables | Podded vegetables | Bulb and stem vegetables | Root and tuberous vegetables |
|---|---|---|---|---|
| Dandelion (*Taraxacum officinale*) | *esculentum* var Tomato | Rice bean (*Vigna umbellatta*) | Welsh onion (*Allium fistulosum*) | Prairie turnip (*Psoralea esculenta*) |
| Endive (*Cichorium endivia*) | Perennial cucumber (*Coccinia grandis*) | Rice (*Vigna umbellatta*) | Wild leek (*Allium tricoccum*) | Radish (*Raphanus sativus*) |
| Epazote (*Chenopodium ambrosioides*) | Pumpkin (*Cucurbita maxima, Cucurbita pepo*) | Runner bean (*Phaseolus coccineus*) | | Rutabaga (*Brassica napus* Napobrassica group) |
| Fat hen (*Chenopodium album*) | Pattypan squash | Soybean (*Glycine max*) | | Salsify (*Tragopogon porrifolius*) |
| Fiddlehead (*Pteridium aquilinum, Athyrium esculentum*) | Snake gourd (*Trichosanthes cucumerina*) | Tarwi (tarhui, chocho; *Lupinus mutabilis*) | | Scorzonera (*Scorzonera hispanica*) |
| Fluted pumpkin (*Telfairia occidentalis*) | Squash (aka marrow) (*Cucurbita pepo*) | Tepary bean (*Phaseolus acutifolius*) | | Skirret (*Sium sisarum*) |
| Golden samphire (*Inula crithmoides*) | Sweetcorn aka corn or maize (*Zea mays*) | Urad bean (*Vigna mungo*) | | Sweet Potato (Kumara) |
| Good King Henry (*Chenopodium bonus-henricus*) | Sweet pepper (*Capsicum annuum* Grossum group) | Velvet bean (*Mucuna pruriens*) | | Taro (*Colocasia esculenta*) |
| Jambu (*Acmella oleracea*) | Tinda (*Praecitrullus fistulosus*) | Winged bean (*Psophocarpus tetragonolobus*) | | Ti (*Cordyline fruticosa*) |
| Kai-lan (*Brassica rapa* Alboglabra group) | Tomatillo (*Physalis philadelphica*) | Yardlong bean (*Vigna unguiculata* subsp. *sesquipedalis*) | | Tigernut (*Cyperus esculentus*) |
| Komatsuna (*Brassica rapa Perviridis* or Komatsuna group) | Winter melon (*Benincasa hispida*) | | | Turnip (*Brassica rapa* Rapifera group) |
| Kuka (*Adansonia* spp.) | West Indian gherkin (*Cucumis anguria*) | | | Ulluco (*Ullucus tuberosus*) |
| Lagos bologi (*Talinum fruticosum*) | Zucchini or Courgette (*Cucurbita pepo*) | | | Wasabi (*Wasabia japonica*) |
| Land cress (*Barbarea verna*) | Globe Artichoke (*Cynara scolymus*) | | | Water chestnut (*Eleocharis dulcis*) |
| Lizard's tail (*Houttuynia cordata*) | Squash blossoms (*Cucurbita* spp.) | | | Yacon (*Smallanthus sonchifolius*) |
| Melokhia (*Corchorus olitorius, Corchorus capsularis*) | Broccoli (*Brassica oleracea*) | | | Yam (*Dioscorea* spp.) |
| Mizuna greens (*Brassica rapa* Nipposinica group) | Cauliflower (*Brassica oleracea*) | | | |
| Mustard (*Sinapis alba*) | | | | |
| Napa/Chinese Cabbage (*Brassica rapa* Pekinensis group) | | | | |
| New Zealand Spinach (*Tetragonia tetragonioides*) | | | | |
| Orache (*Atriplex hortensis*) | | | | |
| Pea sprouts/leaves (*Pisum sativum*) | | | | |
| Polk (*Phytolacca americana*) | | | | |
| Radicchio (*Cichorium intybus*) | | | | |
| Garden Rocket (*Eruca sativa*) | | | | |
| Samphire (*Crithmum maritimum*) | | | | |
| Sea beet (*Beta vulgaris* subsp. *maritima*) | | | | |
| Seakale (*Crambe maritima*) | | | | |
| Sierra Leone bologi (*Crassocephalum* spp.) | | | | |
| Soko (*Celosia argentea*) | | | | |
| Sorrel (*Rumex acetosa*) | | | | |
| Summer purslane (*Portulaca oleracea*) | | | | |
| Swiss chard (*Beta vulgaris* subsp. *cicla* var. *flavescens*) | | | | |
| Tatsoi (*Brassica rapa* Rosularis group) | | | | |
| Turnip greens (*Brassica rapa* Rapifera group) | | | | |

TABLE I-continued

| Leafy and salad vegetables | Fruiting and flowering vegetables | Podded vegetables | Bulb and stem vegetables | Root and tuberous vegetables |
|---|---|---|---|---|
| Watercress (*Nasturtium officinale*) Water spinach (*Ipomoea aquatica*) Winter purslane (*Claytonia perfoliata*) Yau choy (*Brassica napus*) | | | | |

Methods of making the composition

The composition described herein can be prepared by any of the applicable techniques of chemical formulations. Many such techniques are well known in the art. For example, each of the substances of the composition can be contacted with each other, and subsequently mixed, stirred, shaken or otherwise agitated, to achieve a relatively homogeneous mixture. See, e.g., Example 1 herein.

Utility

The composition described herein can be usable, e.g., as a residential sanitizer, commercial sanitizer and/or industrial sanitizer. Specifically, the composition described herein can be usable for antiseptic cleansing of a surface of equipment used in the food industry. Additionally, the composition described herein can be usable, e.g., for antiseptic cleansing of a topical surface of a human or other animal. Specifically, the composition described herein can be usable for a hand sanitizer.

The composition described herein can be applied in any suitable and effective manner. Specifically, the composition can be formulated for application to the intended surface by contacting, dipping, spraying and/or coating the composition to the intended surface.

The presently disclosed subject matter provides for a method of killing or inhibiting a microorganism or pathogen. As used herein, "killing" bacteria refers to bacteria that has been inhibited or inactivated (no longer pathogenic) or killed, as well as removed from the surface of interest (due to, for example, washing with a composition disclosed herein) and thus results in a reduced bacterial count. The method includes contacting the microorganism or pathogen with an effective amount of the composition described herein, for a period of time effective to kill or inhibit the microorganism or pathogen.

The contacting of the microorganism or pathogen with the effective amount of the composition can be in vitro or in vivo. Additionally, the contacting can occur on the surface of the plant (e.g., part of a plant) or mammal (e.g., topical surface of a human).

The microorganism or pathogen can be a bacteria, gram-negative bacteria (including, but not limited to, *Escherichia coli, Salmonella, Shigella, Haemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, and Salmonella typhi*), gram-positive bacteria (including, but not limited to, *Bacillus, Listeria, Staphylococcus, Streptococcus, Enterococcus,* and *Clostridium*), enteric bacteria (including, but not limited to, bacteria from the genera *Bacteroides, Clostridium, Fusobacterium, Eubacterium, Ruminococcus, Peptococcus, Peptostreptococcus, Bifidobacterium, Escherichia and Lactobacillus*), virus (e.g., RNA viruses (e.g., Reoviruses, Picornaviruses, Togaviruses, Orthomyxoviruses, or Rhabdoviruses), DNA viruses (e.g., Adenoviruses, Herpesviruses, Poxviruses, or Parvoviruses), or reverse transcribing viruses (e.g., Retroviruses or Hepadnaviruses)), fungus (including, but not limited to, rice blast fungus (e.g., *Magnaporthe oryzae*), tree pathogens (such as *Ophiostoma ulmi, Ophiostoma novo-ulmi* and *Cryphonectria parasitica*), and plant pathogens (e.g., in the genera *Fusarium, Ustilago, Alternaria,* and *Cochliobolus*, as well as fungi (e.g., *Aspergillus, Candida, Cryptococcus, Histoplasma, Pneumocystis* and dermatophytic and keratinophilic fungi) which can cause diseases in humans, including, but not limited to, aspergilloses, candidoses, coccidioidomycosis, cryptococcosis, histoplasmosis, mycetomas, paracoccidioidomycosis, ringworm and athlete's foot), mold (including, but not limited to, *Acremonium, Aspergillus, Cladosporium, Fusarium, Mucor, Penicillium, Rhizopus, Stachybotrys* or *Trichoderma*), mildew (e.g., mold or fungus, including species of fungi belonging in the order Erysiphales, downy mildew (e.g., caused by fungus-like organisms in the family Peronosporaceae (Oomycota)) or powdery mildew (e.g., the term given to mildew by horticulturalists and gardeners).

The period of time effective to kill or inhibit the microorganism or pathogen can less than about 10 seconds. Alternatively, the period of time effective to kill or inhibit the microorganism or pathogen can be less than about 10 minutes, less than 5 minutes or less than a minute.

The microorganism or pathogen can be selected from *Acinetobacter (Acinetobacter baumannii), Aeromonas (Aeromonas hydrophila), Aspergillus (Aspergillus flavus), Bacillus (Bacillus megaterium, Bacillus cereus), Campylobacter (Cainpylobacter jejuni), Candida (Candida albicans), Clostridium (Clostridium difficile, Clostridium botulinum, Clostridium perfringens* (formerly known as *Clostridium welchii*)), Coronavirus (Human coronavirus 229E (HCoV-229E), Human Coronavirus NL63, Human coronavirus OC43 (HCoV-OC43)), *Corynebacterium (Corynebacterium diphtheriae), Enterobacter (Enterobacter aerogenes), Enterococcus (Enterococcus faecium; Enterococcus faecium* (multi-drug resistant including Vancomycin), *Enterococcus faecalis* (Vancomycin, Streptomycin, and Gentamicin resistant)), *Escherichia (Escherichia coli, Escherichia coli* (ESBL Producing, Multi-drug resistant, derived from clinical isolate, *Klebsiella pneumoniae* ATCC #14714), *Escherichia coli* (0157:H7)); Influenzavirus A, Influenzavirus B, Influenzavirus C, *Klebsiella (Klebsiella pneumoniae), Listeria (Listeria monocytogenes), Listeria (Listeria monocytogenes), Plesiomonas (Plesiomonas shigelloides), Proteus (Proteus mirabilis, Proteus hauseria (vulgaris)), Pseudomonas (Pseudomonas aeruginosa),* Rhinovirus (Human rhinovirus A, Human rhinovirus B), Rotavirus (Rotavirus A, B, or C), *Rhizopus (Rhizopus stolonifer* (black bread mold)), *Salmonella (Salmonella choleraesuis* serotype *typhimurium), Serratia (Serratia marcescens), Shigella (Shigella sonnei),* Simplexvirus (Herpes simplex virus 1 and 2 (HSV-1 and HSV-2)), *Staphylococcus (Staphylococcus aureus* (MRSA), *Staphylo-*

*coccus aureus* (MRSA, Vancomycin tolerant), *Staphylococcus epidermidis*), *Streptococcus* (*Streptococcus pneumoniae* or *pneumococcus, Streptococcus pyogenes*), *Trichophyton* (*Trichophyton mentagrophytes*), *Yersinia* (*Yersinia enterocolitica, Yersinia pseudotuberculosis*) and *Vibrio* (*Vibrio parahaemolyticus, Vibrio cholerae* (Kommabacillus), *Vibrio vulnificus*).

The microorganism or pathogen can be selected from the group of *Alternaria* (*Alternaria arborescens, Alternaria alternata* f.sp. *lycopersici, Alternaria alternata, Alternaria solani, Leveillula taurica, Oidiopsis sicula*), *Botryotinia* (*Botryotinia fuckeliana*), *Athelia* (*Athelia rolfsii*), *Botrytis* (*Botrytis cinerea*), *Ceratocystis* (*Ceratocystis fimbriata*), *Cercospora* (*Cercospora fuligena*), *Chalara* (*Chalara elegans*), *Clavibacter* (*Clavibacter michiganensis* or *michiganensis*), *Colletotrichum* (*Colletotrichum coccodes, Colletotrichum dematium, Colletotrichum gloeosporioides, Glomerella cingulata*), *Corynespora* (*Corynespora cassiicola*), *Didymella* (*Didymella lycopersici*), *Erwinia* (*Erwinia carotovora*), *Fusarium* (*Fusarium oxysporum* f.sp. *radicis-lycopersici, Fusarium oxysporum* f.sp. *lycopersic*), *Geotrichum* (*Geotrichum candidum, Geotrichum klebahnii, G. candidum* var. *citri-aurantii, Galactomyces geotrichum*), *Mycovellosiella* (*Fulvia fulva, Cladosporium fulvum*), *Geotrichum* (*Geotrichum candidum*), *Macrophomina* (*Macrophomina phaseolina*), *Phoma* (*Phoma destructiva*), *Phytophthora* (*Phytophthora capsici, Phytophthora drechsleri, Phytophthora nicotianae* var. *parasitica, Phytophthora parasitica, Phytophthora infestans*), *Pleospora* (*Pleospora tarda, Pleospora herbarum, Pleospora lycopersici*), *Pseudocercospora* (*Pseudocercospora filigen*), *Pseudomonas* (*Pseudomonas syringae* pv., *Pseudomonas corrugata, Pseudomonas syringae* pv. *Syringae*), *Pyrenochaeta* (*Pyrenochaeta lycopersici*), *Pythium* (*Pythium aphanidermatum, Pythium arrhenomanes, Pythium debaryanum, Pythium myriotylum, Pythium ultimum*), *Ralstonia* (*Raistonia solanacearum*), *Rhizoctonia* (*Rhizoctonia solani* and *Thanatephorus cucumeris*), *Rhizopus* (*Rhizopus stolonifer*), *Sclerotinia* (*Sclerotinia sclerotiorum, Sclerotinia minor*), *Sclerotium* (*Sclerotium rolfsii*), *Septoria* (*Septoria lycopersici*), *Stemphylium* (*Stemphylium botryosum, Stemphylium lycopersici, Stemphylium herbarum, Stemphylium consortiale botryosum* f.sp. *lycopersici, Stemphylium floridanum, Stemphylium solani*), *Thielaviopsis* (*Thielaviopsis basicola*), *Ulocladium* (*Ulocladium consortiale*), *Verticillium* (*Verticillium albo-atrum, Verticillium dahliae*), or *Xanthomonas* (*Xanthomonas campestris* pv. *vesicatoria*).

The mammal can be afflicted, or a risk thereof, with a bacterial disease, viral disease, fungal disease, or symptom associated with the same.

Specifically, the mammal can be afflicted, or at risk thereof, with at least one disease or symptom selected from abdominal cramping, abdominal pain, abscess (brain, and hepatic or splenic abscesses), aspergillosis of the lungs, bacteremia, bloating, blood poisoning, boils, botulism, bronchitis, bronchiolitis, carbuncles, catheter-associated bacteremia, cellulitis folliculitis, cholera, clostridial necrotizing enteritis, conjunctivitis, constipation, corneal ulcer, cough, dermatitis (blistering dermatitis), diarrhea (e.g., antibiotic-associated diarrhea (AAD)), digestive problems, diphtheria, encephalitis, emphysematous cholecystitis, endocarditis, endophthalmitis, enteritis, entero-colitis, ecthyma gangrenosum, erythema nodosum, fever, food poisoning, Fried Rice Syndrome, furuncles, gangrene, gastroenteritis (e.g., rotavirus gastroenteritis), hæmolytic-uremic syndrome (HUS), headache, ileitis, impetigo, infarction, infection (of the lungs (respiratory tract infections), infection of airway epithelial cells, lower respiratory tract infections), corneal, otomycotic, and nasoorbital infections, oral and genital infections, urinary tract infection, wound infections, staph infection, surgical wound infection, wound infections, infections in skin and other tissues, bladder, prostate, tear duct infections, epididymal infections, and intrauterine or cervical infections), inflammation, influenza, keratitis, kidney stones, laryngitis, listeriosis, lymphadenopathy, malaise, meningitis (bacterial meningitis, neonatal meningitis), meningoencephalitis, mastitis, mesenteric adenitis, muscle pains, myonecrosis, nausea, oral herpes, osteomyelitis (osteomyelitis endocarditis), otitis (e.g., otitis media), pink eye, paratyphoid fever, pericarditis, peritonitis, Peyer's patch necrosis, pharyngitis (strep throat), pimples, pseudomembranous colitis, pneumonia (e.g., Gram-negative pneumonia), red eyes, rhinitis, rhinorrhoea, runny or blocked nose salmonellosis, sepsis, septic arthritis, septicemia, scalded skin syndrome, shigellosis, sinusitis, sneezing, sore throat, tissue necrosis, toxic shock syndrome (TSS), typhoid fever, vomiting, and yeast infections.

The plant may be afflicted, or at risk thereof, with a bacterial disease, a fungal disease, or a symptom associated with the same.

Specifically, the plant can be afflicted, or at risk thereof, with at least one disease or symptom selected from the group of Bacterial canker, Bacterial speck, Bacterial spot, Bacterial stem rot and fruit rot, Bacterial wilt, Pith necrosis, Syringae leaf spot, *Alternaria* stem canker, Anthracnose, Black mold rot, Black root rot, Black shoulder, Buckeye fruit and root rot, *Cercospora* leaf mold, Charcoal rot, Corky root rot, Didymella stem rot, Early blight, *Fusarium* crown and root rot, *Fusarium* wilt, Gray leaf spot, Gray mold, Late blight, Leaf mold, Phoma rot, Powdery mildew, *Pythium* damping-off and fruit rot, Rhizoctonia damping-off and fruit rot, *Rhizopus* rot, *Septoria* leaf spot, Sour rot, Southern blight, Target spot, *Verticillium* wilt and White mold.

The presently disclosed subject matter also provides for a method of washing a plant. The method includes contacting the plant with an effective amount of the composition described herein, for a period of time effective to wash the plant.

An edible part of the plant can be washed. Additionally, the plant can be washed before harvesting. Alternatively, the plant can be washed after harvesting.

The period of time effective to wash the plant can be less than about 10 seconds. Alternatively, the period of time effective to wash the plant can be less than about 10 minutes, less than 5 minutes or less than a minute.

The presently disclosed subject matter also provides for a method of washing a surface of equipment used in the food industry. The method includes contacting the surface with an effective amount of the composition described herein, for a period of time effective to wash the surface.

The presently disclosed subject matter also provides for a method of disinfecting a surface of equipment used in the food industry. The method includes contacting the surface with an effective amount of the composition described herein, for a period of time effective to disinfect the surface.

The equipment used in the food industry can include packaging material, a packaging facility, a refrigeration device, a storage device, the inside of a transportation vehicle, a belt or conveyor used to transport fruits or vegetables, a bin or gondola used to transport produce, a bucket or pail used to harvest fruits or vegetables, a plastic clam shell, a pint basket, or a knife or cutting device used in the harvest of fruits or vegetables. In one specific embodiment, the food preparation surface (e.g., a cooking surface) or the food storage surface can include at least one of a refrigerator, a freezer, an oven, a stove, a countertop, a cutting board, a microwave oven, a sink, a cooking range, a grill, a cooktop, a ventilation hood, a cooking pot, a cooking pan, a frying pan, a roasting pan, a mixing bowl and a cooking utensil.

The presently disclosed subject matter also provides for a method of cleaning a food preparation surface (e.g., a cooking surface) or a food storage surface. The method includes contacting the surface with an effective amount of the composition described herein, for a period of time effective to clean the surface.

The presently disclosed subject matter also provides for a method of disinfecting a food preparation surface (e.g., a cooking surface) or a food storage surface. The method includes contacting the surface with an effective amount of the composition described herein, for a period of time effective to disinfect the surface.

The food preparation surface (e.g., a cooking surface) or the food storage surface can be present in a residential dwelling, e.g., in a kitchen of a personal dwelling. Alternatively, the food preparation surface (e.g., a cooking surface) or the food storage surface can be present in a commercial building, e.g., in a kitchen of a restaurant.

The presently disclosed subject matter also provides for a method of washing a surface present in a hospital, health clinic or nursing home. The method includes contacting the surface with an effective amount of the composition described herein, for a period of time effective to wash the surface.

The presently disclosed subject matter also provides for a method of disinfecting a surface present in a hospital, health clinic or nursing home. The method includes contacting the surface with an effective amount of the composition described herein, for a period of time effective to disinfect the surface.

The methods described herein can further include the use of a disinfectant, in combination with the composition described herein. In such a situation, the use of the disinfectant can be concurrent with the use of the composition described herein, or can be sequential with the use of the composition described herein.

The compositions described herein can be used in combination with other substances for their intended uses described herein. For example, when used to kill or inhibit a microorganism or a pathogen, the compositions described herein can be used in combination with other substances known to kill or inhibit a microorganism or a pathogen. When used to wash a plant, the compositions described herein can be used in combination with other substances known to wash plants. When used to wash a surface of equipment used in the food industry or a surface in a food packaging facility, the compositions described herein can be used in combination with other substances known to wash a surface of equipment used in the food industry or a surface in a food packaging facility. Additionally, when used to clean or disinfect a food preparation surface (e.g., a cooking surface) or a food storage surface, the compositions described herein can be used in combination with other substances known to clean or disinfect a food preparation surface (e.g., a cooking surface) or a food storage surface. In each of the situations above, the compositions described herein can independently be used at the same time (i.e., simultaneously) as the other substance(s), or can be used sequentially with the other substance(s).

The compositions described herein can have suitable biological activity against any one or more of the organisms and/or diseases described in Table II below.

TABLE II

| Organisms | | |
|---|---|---|
| Genus | Species | Diseases (examples) |
| Acinetobacter | Acinetobacter baumannii | Pneumonia, meningitis, septicemia, urinary and respiratory tract infections. |
| Aeromonas | Aeromonas hydrophila | Human diarrhea, cellulitis, myonecrosis, and ecthyma gangrenosum. |
| Aspergillus | Aspergillus flavus | Infarction. |
| Bacillus | Bacillus megaterium | Bacillus megaterium is considered non-pathogenic, but forming endospores can contaminate just about anything that is not maintained in a sterile environment. |
| | Bacillus cereus | foodborne illness, Fried Rice Syndrome, diarrheal and emetic vomiting syndrome. |
| Campylobacter | Campylobacter jejuni | Food poisoning, enteritis, abdominal pain, diarrhea, fever, and malaise. |
| Candida | Candida albicans | Yeast infections |
| Clostridium | Clostridium difficile | Antibiotic-associated diarrhea AAD, pseudomembranous colitis, bloating, constipation, and diarrhea with abdominal pain. |
| | Clostridium botulinum. | human botulism |
| | Clostridium perfringens formerly known as Clostridium welchii | Tissue necrosis, bacteremia, emphysematous cholecystitis, and gas gangrene, which is also known as clostridial myonecrosis. Manifestations typically include abdominal cramping and diarrhea - vomiting and fever are unusual. Very rare, fatal cases of clostridial necrotizing enteritis have been known to involve "Type C" strains of the organism, which produce a potently ulcerative β-toxin. |
| Coronavirus | Human coronavirus 229E HCoV-229E | Infection of airway epithelial cells. |
| | Human Coronavirus NL63 | Bronchiolitis |
| | Human coronavirus OC43 HCoV-OC43 | Fever, cough, sore throat, digestive problems, rhinitis, rhinorrhoea, pharyngitis, laryngitis, otitis, bronchitis, bronchiolitis, and pneumonia. Lower respiratory tract-infections. |
| Corynebacterium | Corynebacterium diphtheriae | Diphtheria |
| Enterobacter | Enterobacter aerogenes | E. aerogenes is a nosocomial and pathogenic bacterium that causes opportunistic infections in skin and other tissues |
| Enterococcus | Enterococcus faecium | E. faecium is a pathogen that causes nosocomial bacteremia, surgical wound infection, endocarditis, and urinary tract infections. |
| | Enterococcus faecium multi-drug resistant including Vancomycin | E. faecium is a pathogen that causes nosocomial bacteremia, surgical wound infection, endocarditis, and urinary tract infections. |

TABLE II-continued

| | Organisms | |
|---|---|---|
| Genus | Species | Diseases (examples) |
| | *Enterococcus faecalis* Vancomycin Streptomycin and Gentamicin resistant | *E. faecalis* can cause endocarditis, as well as bladder, prostate, and epididymal infections. |
| *Escherichia coli* | *Escherichia coli* ESBL Producing Multi-drug resistant derived from clinical isolate *Klebsiella pneumoniae* ATCC #14714 | Gastroenteritis, urinary tract infections, and neonatal meningitis. In rarer cases, virulent strains are also responsible for haemolytic-uremic syndrome (HUS), peritonitis, mastitis, septicemia and Gram-negative pneumonia. |
| | *Escherichia coli* O157:H7; | Gastrointestinal illness<br>*E. coli* O157:H7 infection often causes severe, acute bloody diarrhea although non-bloody diarrhea is also possible and abdominal cramps. Usually little or no fever is present, and the illness resolves in 5 to 10 days. It can also be asymptomatic. |
| Influenzavirus | Influenzavirus A | Influenza; common symptoms of the disease are chills and fever, pharyngitis, muscle pains, severe headache, coughing, weakness and general discomfort. |
| | Influenzavirus B | Influenza; common symptoms of the disease are chills and fever, pharyngitis, muscle pains, severe headache, coughing, weakness and general discomfort. |
| | Influenzavirus C | Influenza; common symptoms of the disease are chills and fever, pharyngitis, muscle pains, severe headache, coughing, weakness and general discomfort. |
| *Klebsiella* | *Klebsiella pneumoniae* | *K. pneumoniae* can cause bacterial pneumonia. |
| *Listeria* | *Listeria monocytogenes* | *L. monocytogenes* causes the disease listeriosis. The manifestations of listeriosis include septicemia, meningitis or meningoencephalitis, encephalitis, corneal ulcer, pneumonia, and intrauterine or cervical infections in pregnant women, which may result in spontaneous abortion 2nd/3rd trimester or stillbirth. |
| *Plesiomonas* | *Plesiomonas shigelloides* | Gastroenteritis is the disease with which *P. shigelloides* has been implicated. *P. shigelloides* gastroenteritis is usually a mild self-limiting disease with fever, chills, abdominal pain, nausea, diarrhea, or vomiting |
| *Proteus* | *Proteus mirabilis* | This rod shaped bacterium has the ability to produce high levels of urease. Urease hydrolyzes urea to ammonia NH$_3$ and thus makes the urine more alkaline. If left untreated, the increased alkalinity can lead to the formation of crystals of struvite, calcium carbonate, and/or apatite.<br>*Proteus* can also cause wound infections, septicemia and pneumonias. |
| | *Proteus hauseria vulgaris* | It is known to cause urinary tract infections and wound infections. |
| *Pseudomonas* | *Pseudomonas aeruginosa* | Inflammation and sepsis. Dermatitis |
| Rhinovirus | Human rhinovirus A | Runny or blocked nose, sneezing, a sore throat, a dry cough, red eyes and a general feeling of tiredness. |
| | Human rhinovirus B | Runny or blocked nose, sneezing, a sore throat, a dry cough, red eyes and a general feeling of tiredness. |
| | Human rhinovirus C | Febrile wheeze and asthmatic exacerbations. |
| Rotavirus | Rotavirus A | Rotavirus A infections can occur throughout life: the first usually produces symptoms, but subsequent infections are typically asymptomatic, Rotavirus gastroenteritis is a mild to severe disease characterized by vomiting, watery diarrhoea, and low-grade fever. |
| | B | adult diarrhea |
| | C | Rotavirus C has been associated with rare and sporadic cases of diarrhoea |
| | D | |
| | E | |
| | or F | |
| *Rhizopus* | *Rhizopus stolonifer* black bread mold | |
| *Salmonella* | *Salmonella choleraesuis* serotype typhimurium | Blood poisoning |
| *Serratia* | *Serratia marcescens* | *S. marcescens* is involved in nosocomial infections, particularly catheter-associated bacteremia, urinary tract infections and wound infections, and is responsible for 1.4% of nosocomial bacteremia cases in the United States. It is commonly found in the respiratory and urinary tracts of hospitalized adults and in the gastrointestinal system of children.<br>*Marcescens* can cause infection in several sites, including the urinary tract, respiratory tract, wounds, and the eye, where it may cause conjunctivitis, keratitis, endophthalmitis, and tear duct infections. It is also a rare cause of endocarditis and osteomyelitis particularly in those who use intravenous drugs recreationally, pneumonia, and meningitis. |
| *Shigella* | *Shigella sonnei* | Shigellosis.<br>dysenteric diseases. The most common symptom is bloody stool and small to severe diarrhea. Other symptoms on some people are mild to high fever, malaise, and tenesmus. |
| Simplexvirus | Herpes simplex virus 1 and 2 HSV-1 and HSV-2 | Oral herpes, the visible symptoms of which are colloquially called cold sores, infects the face and mouth. Oral herpes is the most common form of infection. Infection of the genitals, commonly known as herpes, is the second most common form of herpes. Other disorders such as herpetic whitlow, herpes gladiatorum, ocular herpes keratitis, cerebral herpes infection encephalitis, Mollaret's meningitis, neonatal herpes, and possibly Bell's palsy are all caused by herpes simplex viruses. |

TABLE II-continued

| Organisms | | |
|---|---|---|
| Genus | Species | Diseases (examples) |
| Staphylococcus | Staphylococcus aureus MRSA | S. aureus can cause a range of illnesses from minor skin infections, such as pimples, impetigo may also be caused by Streptococcus pyogenes, boils, cellulitis folliculitis, furuncles, carbuncles, scalded skin syndrome and abscesses, to life-threatening diseases such as pneumonia, meningitis, osteomyelitis endocarditis, Toxic shock syndrome TSS, and septicemia. Its incidence is from skin, soft tissue, respiratory, bone, joint, endovascular to wound infections. It is still one of the four most common causes of nosocomial infections, often causing postsurgical wound infections. |
| | MRSA Vancomycin tolerant | S. aureus can cause a range of illnesses from minor skin infections, such as pimples, impetigo may also be caused by Streptococcus pyogenes, boils, cellulitis folliculitis, furuncles, carbuncles, scalded skin syndrome and abscesses, to life-threatening diseases such as pneumonia, meningitis, osteomyelitis endocarditis, Toxic shock syndrome TSS, and septicemia. Its incidence is from skin, soft tissue, respiratory, bone, joint, endovascular to wound infections. It is still one of the four most common causes of nosocomial infections, often causing postsurgical wound infections. |
| | Staphylococcus epidermidis | Staphylococcus epidermidis strains represent the most frequent cause of nosocomial sepsis and the most common agents of infections with implanted medical devices. |
| Streptococcus | Streptococcus pneumoniae or pneumococcus | the organism causes many types of pneumococcal infection other than pneumonia, including acute sinusitis, otitis media, meningitis, bacteremia, osteomyelitis, septic arthritis, endocarditis, peritonitis, pericarditis, cellulitis, and brain abscess. |
| | Streptococcus pyogenes | S. pyogenes is the cause of many important human diseases ranging from mild superficial skin infections to life-threatening systemic diseases. Infections typically begin in the throat or skin. Examples of mild S. pyogenes infections include pharyngitis "strep throat" and localized skin infection "impetigo". Erysipelas and cellulitis are characterized by multiplication and lateral spread of S. pyogenes in deep layers of the skin. S. pyogenes invasion and multiplication in the fascia can lead to necrotizing fasciitis, a potentially life-threatening condition requiring surgical treatment. |
| Trichophyton | Trichophyton mentagrophytes | Known as 'Malabar itch', a skin infection consisting of an eruption of a number of concentric rings of overlapping scales forming papulosquamous patches is caused by the fungus. |
| Yersinia | Yersinia enterocolitica | Acute Y. enterocolitica infections produce severe diarrhea in humans, along with Peyer's patch necrosis, chronic lymphadenopathy, and hepatic or splenic abscesses. Additional symptoms may include entero-colitis, fever, mesenteric adenitis, erythema nodosum and acute terminal ileitis. |
| | Yersinia pseudotuberculosis | In animals, Y. pseudotuberculosis can cause tuberculosis-like symptoms, including localized tissue necrosis and granulomas in the spleen, liver, and lymph node. Symptoms are similar to those of infection with Y. enterocolitica fever and right-sided abdominal pain, except that the diarrheal component is often absent, which sometimes makes the resulting condition difficult to diagnose. Y. pseudotuberculosis infections can mimic appendicitis, especially in children and younger adults, and, in rare cases the disease may cause skin complaints erythema nodosum, joint stiffness and pain reactive arthritis, or spread of bacteria to the blood bacteremia. |
| Vibrio | Vibrio parahaemolyticus | watery diarrhea accompanied by nausea, vomiting, abdominal cramps, and sometimes fever. |
| | Vibrio cholerae Kommabacillus | Cholera |
| | Vibrio vulnificus. | Symptoms include vomiting, diarrhea, abdominal pain, and a blistering dermatitis. |

Obviously, numerous modifications and variations of the presently disclosed subject matter are possible in light of the above teachings. It is therefore to be understood that within the scope of the appended claims, the disclosed subject matter may be practiced otherwise than as specifically described herein.

Any patent, patent document, or reference disclosed herein is incorporated into reference into this disclosed subject matter and forms part of this disclosed subject matter. The presently disclosed subject matter may be illustrated by the following non-limiting examples.

EXAMPLES

Example 1

Preparation of Composition—EQ Ag Formula "B" Product (Test Substance/Product)

The desired vessel for the mixing the components of Formula B should contain a device for mixing or agitation.

The slow addition of caustic soda (sodium hydroxide, (NaOH)) to the total volume of water (H2O) is desired to maintain a minimal exothermal reaction. The caustic soda (23.2 g) is diluted in water (1280 ml) and agitated for a short period of time, 3-6 minutes until completely combined with the water. Biosoft s-101 (176.6 g) is then added in a steady, consistent manner, for approx. 3-6 minutes until it also is completely diluted in the mixture. Niaproof 08 (520 g) is then added at a steady and consistent manner, for 3-6 minutes and agitated until all is completely blended. The mixture is then left to stand for 24 hours, to ensure total blending of the product. The end result is 2000 ml of product.

Example 2

Evaluation of the Time Kill Kinetics of Antimicrobial Activity of the EQ Ag Formula "B" Product against Gram Negative *Salmonella typhimurium* and Gram Positive *Staphylococcus aureus*

Materials and Methods
Culture Media:
  Nutrient Broth (BBL) was prepared according to manufacturer's directions (such as from Remel (Lenexa, Kans.), Baltimore Biological Labs or BD (Becton, Dickinson and Company, Franklin Lakes, N.J., USA)). 10 ml quantities were dispensed into 20×150 mm test tubes, capped and autoclaved for 20 minutes at 121° C.
  Nutrient Agar (BBL) was prepared according to manufacturer's directions (such as from Remel (Lenexa, Kans.), Baltimore Biological Labs or BD (Becton, Dickinson and Company, Franklin Lakes, N.J., USA)). 10 ml quantities were dispensed into 20×150 mm test tubes, capped and autoclaved for 20 minutes at 121° C. Slanted until cooled and solidified.
Subculture Media:
  Tryptone Glucose Extract Agar (BBL) was prepared according to manufacturer's directions (such as from Remel (Lenexa, Kans.), Baltimore Biological Labs or BD (Becton, Dickinson and Company, Franklin Lakes, N.J., USA)). Dispensed in quantities suitable for easy handling and aseptic technique. Autoclaved for 20 minutes at 121° C.
  FCD Broth (BBL) comprises pancreatic digest of casein (20 g; Remel (Lenexa, Kans.)), soy lecithin (10 g; Sigma Aldrich (St. Louis, Mo.), polysorbate 20 (40 ml; polysorbate 80 (Sigma Aldrich) may also be used), Na2 thiosulfate (5 g; Sigma Aldrich), Triton X-100 (1 ml; Sigma Aldrich) and purified water (960 ml). FCD broth was prepared by dissolving the pancreatic digest of casein and soy lecithin in 960 ml of water, heating in a water bath at about 48° C. to about 50° C. for about 30 minutes. Then polysorbate, Na2thiosulfate, Triton X-100 and water were added. The broth was then mixed, dispensed in 99 ml quantities into milk dilution bottles or 9 mls into 25×150 ml test tubes (modified procedure) and autoclaved for about 20 minutes at about 121° C.
Reagents and Apparatus
  Phenol Coefficient Method (a measure of the bactericidal activity of a chemical compound in relation to phenol), AOC 14: Chapter 4, pg. 65 (further discussed below).
1. Phenol Stock Solution (5% W/V)
2. Phosphate Buffer Stock (0.25 m)
   34.0 g $KH_2PO_4$ was dissolved in 500 ml of Milli-Q water and adjusted to pH 7.2 with 1N NaOH and diluted to 1 L.
3. Phosphate Buffer Dilution Water
   1.25 ml of 0.25M phosphate buffer stock was added to 1 L of Milli-Q water and mixed. Dispensed in 99 ml portions in milk dilution bottles. Autoclaved for 20 minutes at 121° C.
4. Glassware
   50 ml beakers with magnetic stir bars were covered with aluminum foil and sterilized for 20 minutes at 121° C. For modified study, sterile disposable 50 ml centrifuge tubes (Baxter Cat. No. C3920-50A or equivalent) were used.
5. Petri Dishes
   Sterile disposable petri dishes 15×100 mm.
6. Pipettes
   Sterile disposable pipettes.
7. Transfer Loops
   Transfer loops were held in a suitable holder with a 4 mm diameter of Platinum-rhodium, 1 inch long and bent at a 30-degree angle and were used, for example, in volume transfer during testing. Suitable metal or plastic disposable transfer loops were used, for example, during daily culture transfer.
8. Magnetic Stir Plate
9. Vortex Mixer (modified procedure)
Test Systems
  *Salmonella typhimurium* (ATCC No. (14028))
  *Staphylococcus aureus* (ATCC No. (6538)
  Maintained on nutrient agar slants by monthly transfers. Slants stored at 4° C. From the stock culture a tube of nutrient broth was inoculated and about 3 consecutive 24 hour transfers in nutrient broth incubated at 37° C.+/−2° C. centigrade were made before using the culture for testing. 22-26 hour broth culture of organisms grown in nutrient broth at 37° C.±2° C. was vortexed and allowed to settle for 15 minutes prior to testing.
Controls
  Negative Controls for all medias were performed by incubation of uninoculated media. Positive Controls were performed for all organisms by plating directly onto the appropriate media employed for the assay. Broths were tested for Positive growth by inoculation with the appropriate organism.
Operating Technique—Time Kill Study
1. 10 ml of antibacterial test product was placed in 50 ml beaker and placed on a magnetic stir plate. Speed of mixer was adjusted for rapid mixing without creating air bubbles.
2. 0.2 ml of test organism was added to antibacterial test product.
3. After each desired exposed time (such as 15, 30 or 60 seconds), 1.0 ml of inoculated antibacterial test product was removed and subcultured into 99 ml of FCD Broth. This represents a 10 to the −2 dilution. Subcultured again from first bottle of FCD Broth to second bottle of FCD Broth. This represents a 10 to the −4 dilution.
4. Enumerated by serial dilutions and pour plate technique. (For antibacterial test product, 10 to the −2, 10 to the −3, 10 to the −4 were plated in duplicate.)
5. For each test organism tested, initial test organism numbers were determined. This was accomplished by replacing 10 ml of antibacterial soap with 10 ml phosphate buffer and repeating steps 1-4 with the exception of exposure time. (10 to the −5 and 10 to the −6 were plated in triplicate for # control.)
Operating Technique—Modified Time Kill Study
  10 ml of the test substance was placed into a 50 ml centrifuge tube. The test substance in the tube was allowed to equilibrate to test temperature for 40 minutes. 0.2 ml of a 24-hour broth culture was added to 10 ml of the test substance and vortexed vigorously for 10 seconds. Fifteen seconds after adding the suspension, 1 ml of the test substance/culture suspension mixture was removed with a 1 ml syringe and transferred to 9 ml of neutralizer (a 10 to the −1 dilution). The same procedure was repeated for the 30-second exposure. 1 ml from the initial neutralizer (a 10 to the −2 dilution) was transferred. Both 10 to the −2 and 10 to the −3 dilutions from the second neutralizer tube were plated by adding 1 ml and 0.1 ml respectively to separate petri plates. 1 ml of the 10 to the −2 was diluted into 99 ml of phosphate buffered dilution water (PBDW) to result in a 10 to the −4 dilution. 1 ml of the 10 to the −4 dilution was added to a petri plate. The pour plate technique was used with the subculture medium for enumeration of survivors. Inoculum numbers were enumerated by adding 0.2 ml of the 24-hour broth culture to 10 ml of PBDW, vortexed and then serially diluting in PBDW. Enumeration was also carried out using pour plate technique on 10 to the −5 and 10 to the −6 dilutions. All plates were incubated for 48 hours at 37° C.±2° C. (Time Kill Study and Modified Time Kill Study Protocol CFR, Vol. 59, No. 116, Section 333.470 Official Methods of Analysis (15th Ed.), Association of Official Analytical Chemists, Arlington, Va. 199).

Calculation

I=Initial Bacterial Suspension Count

S=Survivors (Test Substance) Count $$\% R = I-s/I \times 100$$

Results were reported as a % reduction in relationship to exposure time.

Controls

1. Phenol Resistance Method

From the 5% phenol stock solution, the appropriate dilutions for the culture to be tested were made. Test tubes containing 5 ml of each dilution to be tested were placed in a 20° C. water bath for 10 minutes. 0.5 ml of test culture was added to the first dilution of phenol and 30 seconds later the second dilution was seeded and so on until 4.5 minutes have passed. After adding the culture, the tubes were gently agitated to distribute the bacteria. Five minutes after seeding the first test tube, one loop full of phenol culture mixture was transferred to a subculture tube. This procedure was repeated until all tubes were transferred after 5, 10 and 15 minutes exposure. The subculture tubes were incubated at 37° C.±2° C. centigrade for 48 hours.

2. Neutralization Method

Procedures performed in duplicate.

Time Kill Study:

The following solutions were inoculated with 0.1 ml of a 10 to the −3 dilution of the test system.

a. 99 ml neutralizer+1 ml test substance use-solution b. 99 ml neutralizer+1 ml test substance dilution c. 100 ml phosphate Buffer Dilution Water After a 10 minute contact time, the bacteria were enumerated using serial dilutions and pour plate technique. The plates were incubated at 37° C. for 48 hours (or at an appropriate temperature for growth of the test system).

Modified Time Kill Study:

The following solutions were inoculated with 0.1 ml of a 10 to the −3 dilution of the test system.

a. 9 ml neutralizer+1 ml test substance use-solution b. 9 ml neutralizer+1 ml test substance dilution c. 10 ml phosphate Buffer Dilution Water After a 10 minute contact time, the bacteria were enumerated using serial dilutions and pour plate technique. The plates were incubated at 37° C. for 48 hours (or at an appropriate temperature for growth of the test system).

The neutralizer is effective if a=b. The neutralizer is not detrimental to the test system if b=c.

3. Sterile FCD Broth 1 ml of FCD broth (prepared as discussed above) was plated for this test.

4. Sterile Phosphate Buffer Dilution Water 1 ml of sterile phosphate buffer was plated for this test.

Results

1. TEST Product—EQ Ag Formula "B" Diluted 1:200 Water
   Salmonella typhimurium (ATCC No. 14028)
   Sample Data Results Percent Reduction indicated for test time points.

Note: NG=No Growth Detected at 48 hours incubation
  G=Growth Detected at 48 hours incubation

| Average Initial Bacterial Counts = $63.6 \times 10^7$ cts per 0.2 ml | | | |
|---|---|---|---|
| Time Point | Initial Population | Average Survival (CFU) | Average Percent Reduction |
| 30 seconds | $63.6 \times 10^7$ | $38.0 \times 10^4$ | 99.94% |
| 1 minute | $63.6 \times 10^7$ | $31.0 \times 10^4$ | 99.95% |
| 5 minutes | $63.6 \times 10^7$ | $31.5 \times 10^4$ | 99.95% |
| 10 minutes | $63.6 \times 10^7$ | $31.0 \times 10^4$ | 99.95% |
| 15 minutes | $63.6 \times 10^7$ | $35.0 \times 10^4$ | 99.94% |
| Positive Controls | G | G | G |
| Negative Controls | NG | NG | NG |

Note: Time Kill Value represents procedures performed in quadruplicate for the determination of the Bacteriological Kinetics.

2. TEST Product—EQ Ag Formula "B" Diluted 1:400 Water
   Salmonella typhimurium (ATCC No. 14028)
   Sample Data Results Percent Reduction indicated for test time points.

Note: NG=No Growth Detected at 48 hours incubation
  G=Growth Detected at 48 hours incubation

| Average Initial Bacterial Counts = $63.6 \times 10^7$ cts per 0.2 ml | | | |
|---|---|---|---|
| Time Point | Initial Population | Average Survival (CFU) | Average Percent Reduction |
| 30 seconds | $63.6 \times 10^7$ | $71.5 \times 10^4$ | 99.89% |
| 1 minute | $63.6 \times 10^7$ | $65.0 \times 10^4$ | 99.90% |
| 5 minutes | $63.6 \times 10^7$ | $49.0 \times 10^4$ | 99.92% |
| 10 minutes | $63.6 \times 10^7$ | $33.5 \times 10^4$ | 99.95% |
| 15 minutes | $63.6 \times 10^7$ | $35.0 \times 10^4$ | 99.94% |
| Positive Controls | G | G | G |
| Negative Controls | NG | NG | NG |

Note: Time Kill Value represents procedures performed in quadruplicate for the determination of the Bacteriological Kinetics.

3. TEST Product—EQ Ag Formula "B" Diluted 1:200 Water+50 PPM Free Chlorine
   Salmonella typhimurium (ATCC No. 14028)
   Sample Data Results Percent Reduction indicated for test time points.

Note: NG=No Growth Detected at 48 hours incubation
  G=Growth Detected at 48 hours incubation

| Average Initial Bacterial Counts = $62.1 \times 10^7$ cts per 0.2 ml | | | |
|---|---|---|---|
| Time Point | Initial Population | Average Survival (CFU) | Average Percent Reduction |
| 30 seconds | $62.1 \times 10^7$ | 1.0 | 99.999% |
| 1 minute | $62.1 \times 10^7$ | 1.0 | 99.999% |
| 5 minutes | $62.1 \times 10^7$ | 1.0 | 99.999% |
| 10 minutes | $62.1 \times 10^7$ | 1.0 | 99.999% |
| 15 minutes | $62.1 \times 10^7$ | 1.0 | 99.999% |
| Positive Controls | G | G | G |
| Negative Controls | NG | NG | NG |

Note: Time Kill Value represents procedures performed in quadruplicate for the determination of the Bacteriological Kinetics.
4. TEST Product—EQ Ag Formula "B" Diluted 1:600 Water
   *Salmonella typhimurium* (ATCC No. 14028)
   Sample Data Results
Percent Reduction indicated for test time points.
Note: NG=No Growth Detected at 48 hours incubation
   G=Growth Detected at 48 hours incubation Average Initial Bacterial Counts = $90.5 \times 10^7$ cts per 0.2 ml

| Time Point | Initial Population | Average Survival (CFU) | Average Percent Reduction |
|---|---|---|---|
| 30 seconds | $90.5 \times 10^7$ | $665.0 \times 10^3$ | 99.93% |
| 1 minute | $90.5 \times 10^7$ | $498.5 \times 10^3$ | 99.95% |
| 5 minutes | $90.5 \times 10^7$ | $498.0 \times 10^3$ | 99.95% |
| 10 minutes | $90.5 \times 10^7$ | $438.5 \times 10^3$ | 99.96% |
| 15 minutes | $90.5 \times 10^7$ | $413.0 \times 10^3$ | 99.96% |
| Positive Controls | G | G | G |
| Negative Controls | NG | NG | NG |

Note: Time Kill Value represents procedures performed in quadruplicate for the determination of the Bacteriological Kinetics.
5. TEST Product—EQ Ag Formula "B" Diluted 1:600 Water
   *Staphylococcus aureus* (ATCC No. 6538)
   Sample Data Results
Percent Reduction indicated for test time points.
Note: NG=No Growth Detected at 48 hours incubation
   G=Growth Detected at 48 hours incubation Average Initial Bacterial Counts = $67.7 \times 10^7$ cts per 0.2 ml

| Time Point | Initial Population | Average Survival (CFU) | Average Percent Reduction |
|---|---|---|---|
| 30 seconds | $67.7 \times 10^7$ | $346.0 \times 10^3$ | 99.95% |
| 1 minute | $67.7 \times 10^7$ | $346.0 \times 10^3$ | 99.95% |
| 5 minutes | $67.7 \times 10^7$ | $308.0 \times 10^3$ | 99.95% |
| 10 minutes | $67.7 \times 10^7$ | $258.0 \times 10^3$ | 99.96% |
| 15 minutes | $67.7 \times 10^7$ | $237.0 \times 10^3$ | 99.96% |
| Positive Controls | G | G | G |
| Negative Controls | NG | NG | NG |

Note: Time Kill Value represents procedures performed in quadruplicate for the determination of the Bacteriological Kinetics.
Discussion The EQ Ag Formula "B" Product is consistently effective in exerting greater than a three (3) log bacterial reduction when tested against *Salmonella typhimurium*. The EQ Ag Formula B exhibited a greater than three (3) log reduction when assayed against *Staphylococcus aureus*. The EQ Ag Formula "B" Product is effective in concentrations of 1:200 through a dilution range of 1:600 in having a continued effectiveness in exerting. On-Contact Bactericidal Activity against *Salmonella typhimurium*. The reductions were consistent with a "plateau" like kinetics as related to EQ Ag Formula "B" Product concentration.

The bactericidal properties of the EQ Ag Formula "B" Product is significantly potentiated in the presence of low levels of Chlorine, 50 ppm, in effectively exerting greater than a five (5) log bacterial reduction when tested against *Salmonella typhimurium*. Note, bactericidal activity in the complete reduction of the *Salmonella typhimurium* bacterial inoculum was as early as 30 seconds.

Example 3

The Time Kill Kinetics of Antimicrobial activity of the EQ Ag Fruit & Vegetable Wash (EQ Ag Formula B) against Gram Negative (*Staphylococcus, Pseudomonas* and *Salmonella*) bacterial test organisms was tested. The Modified Time Kill Assay was designed to show the kinetics of rapid kill associated with the product (EQ Ag Formula B). A Neutralizing solution was tested to determine that any residual product was inactivated when the time assay point was plated onto Microbial growth agar.
Materials and Methods
Culture Media
Nutrient Broth (BBL) was prepared according to manufacturer's directions (see above). 10 ml quantities were dispensed into 20×150 mm test tubes, capped, and autoclaved for 20 minutes at 121° C.
Nutrient Agar (BBL) was prepared according to manufacturer's directions (see above). 10 ml quantities were dispensed into 20×150 mm test tubes, capped and autoclaved for 20 minutes at 121° C. Slanted until cooled and solidified.
Subculture Media
Tryptone Glucose Extract Agar (BBL) was prepared according to manufacturer's directions (see above). Dispense in quantities suitable for easy handling and aseptic technique. Autoclaved for 20 minutes at 121° C.
Letheen Broth (BBL) prepared according to manufacturer's directions (such as from Remel (Lenexa, Kans.), Baltimore Biological Labs or BD (Becton, Dickinson and Company, Franklin Lakes, N.J., USA)). Dispensed in 99 ml quantities into milk dilution bottles or 9 mls into 25×150 ml test tubes (modified procedure). Autoclaved for 20 minutes at 121° C.
Reagents and Apparatus
Phenol Coefficient Method, AOC 14: Chapter 4, pg. 65.
1. Phenol Stock Solution (5% W/V)
2. Phosphate Buffer Stock (0.25 m)
   34.0 g $KH_2PO_4$ was dissolved in 500 ml of Milli-Q water and adjusted to pH 7.2 with 1N NaOH and diluted to 1 L.
3. Phosphate Buffer Dilution Water
   1.25 ml of 0.25M phosphate buffer stock was added to 1L of Milli-Q water and mixed. Dispensed in 99 ml portions in milk dilution bottles. Autoclaved for 20 minutes at 121 ° C.
4. Glassware
   50 ml beakers with magnetic stir bars were covered with aluminum foil and sterilized for 20 minutes at 121° C. For modified study, sterile disposable 50 ml centrifuge tubes (Baxter Cat. No. C3920-50A or equivalent) were used.
5. Petri Dishes
   Sterile disposable petri dishes 15×100 mm.
6. Pipette
   Sterile disposable Pipette.
7. Transfer Loops
   Transfer loops were held in a suitable holder with a 4 mm diameter of Platinum-rhodium, 1 inch long and bent at a 30-degree angle and used, for example, in volume transfer during testing). Suitable metal or plastic disposable transfer loops were used, for example, during daily culture transfer.
8. Magnetic Stir Plate
9. Vortex Mixer (modified procedure)
Test Systems
   *Pseudomonas aeruginosa* (ATCC No. 14028)
   *Staphylococcus aureus* (ATCC No. 6538)
   *Salmonella typhimurium* (ATCC No. 14028)

Maintained on nutrient agar slants by monthly transfers. Slants stored at 4° C. From the stock culture a tube of nutrient broth was inoculated and at least 3 consecutive 24 hour transfers in nutrient broth incubated at 37 degrees±2° C. were made before using the culture for testing. (If only one daily transfer has been missed, it is not necessary to repeat the 3 consecutive transfers). 22-26 hour broth culture of organisms grown in nutrient broth at 37° C.±2° C. was vortexed and allowed to settle for 15 minutes prior to testing.

Controls

Negative controls for all media were performed by incubation of uninoculated media. Positive controls were performed for all organisms by plating directly onto the appropriate media employed for the assay. Broths were tested for positive growth by inoculation with the appropriate organism.

Operating Technique—Time Kill Study 1. 10 ml of antibacterial test product was placed in 50 ml beaker and placed on a magnetic stir plate. Speed of mixer was adjusted for rapid mixing without creating air bubbles.
2. 0.2 ml of test organism was added to antibacterial test product.
3. After each desired exposed time (such as 15, 30 or 60 seconds), 1.0 ml of inoculated antibacterial test product was removed and subcultured into 99 ml of Leethen Broth. This represents a 10 to the −2 dilution. Subcultured again from first bottle of Letheen Broth to second bottle of Letheen Broth. This represents a 10 to the −4 dilution.
4. Enumerated by serial dilutions and pour plate technique. (For antibacterial test product, 10 to the −2, 10 to the −3, 10 to the −4 were plated in duplicate.)
5. For each test organism tested, initial test organism numbers were determined. This was accomplished by replacing 10 ml of antibacterial soap with 10 ml phosphate buffer and repeating steps 1-4 with the exception of exposure time. (10 to the −5, 10 to the −6 were plated in triplicate for # control.)

Operating Technique—Modified Time Kill Study 10 ml of the test substance was placed into a 50 ml centrifuge tube. The test substance in the tube was allowed to equilibrate to test temperature for 40 minutes. 0.2 ml of a 24-hour broth culture was added to 10 ml of the test substance and vortexed vigorously for 10 seconds. Fifteen seconds after adding the suspension, 1 ml of the test substance/culture suspension mixture was removed with a 1 ml. syringe and transferred to 9 ml of neutralizer (a 10 to the −1 dilution). The same procedure was repeated for the 30-second exposure. 1 ml from the initial neutralizer (a 10 to the −2 dilution) was transferred. Both 10 to the −2 and 10 to the −3 dilutions from the second neutralizer tube were plated by adding 1 ml and 0.1 ml respectively to separate petri plates. 1 ml of the 10 to the −2 was diluted into 99 ml of phosphate buffered dilution water (PBDW) to result in a 10 to the −4 dilution. 1 ml of the 10 to the −4 dilution was added to a petri plate. The pour plate technique was used with the subculture medium for enumeration of survivors. Inoculum numbers were enumerated by adding 0.2 ml of the 24-hour broth culture to 10 ml of PBDW, vortexed and then serially diluting in PBDW. Enumeration was also carried out using pour plate technique 10 to the −5 and 10 to the −6 dilutions. All plates were incubated for 48 hours at 37° C.±2° C. (Time Kill Study and Modified Time Kill Study Protocol CFR, Vol. 59, No. 116, Section 333.470 Official Methods of Analysis (15th Ed.), Association of Official Analytical Chemists, Arlington, Va. 1990.)

Calculation

I=Initial Bacterial Suspension Count
S=Survivors (Test Substance) Count $$\% R = I-s/I \times 100$$

Results were reported as a % reduction in relationship to exposure time. In one embodiment, to be an effective Antimicrobial according to this test procedure, >99.99% reduction should be achieved.

Controls

1. Phenol Resistance Method

From the 5% phenol stock solution, make the appropriate dilutions for the culture to be tested were made. Test tubes containing 5 ml of each dilution to be tested were placed in a 20° C. water bath for 10 minutes. 0.5 ml of test culture was added to the first dilution if phenol and 30 seconds later the second dilution was seeded and so on until 4.5 minutes have passed. After adding the culture, the tubes were gently agitated to distribute the bacteria. Five minutes after seeding the first test tube, one loop full of phenol culture mixture was transferred to subculture tube. This procedure was repeated until all tubes were transferred after 5, 10 and 15 minutes exposure. The subculture tubes were incubated at 37° C.±2° C. for 48 hours.

2. Neutralization Method

Procedures performed in duplicate.

For the Time Kill Study:

The following solutions were inoculated with 0.1 ml of a 10 to the −3 dilution of the test system.

a. 99 ml neutralizer+1 ml test substance use-solution
b. 99 ml neutralizer+1 ml test substance dilution
c. 100 ml phosphate Buffer Dilution Water After a 10 minute contact time, the bacteria were enumerated using serial dilutions and pour plate technique. The plates were incubated at 37° C. for 48 hours (or at an appropriate temperature for growth of the test system).

For the Modified Time Kill Study:

The following solutions were inoculated with 0.1 ml of a 10 to the −3 dilution of the test system.

a. 9 ml neutralizer+1 ml test substance use-solution
b. 9 ml neutralizer+1 ml test substance dilution
c. 10 ml phosphate Buffer Dilution Water After a 10 minute contact time, he bacteria were enumerated using serial dilutions and pour plate technique. The plates were incubated at 37° C. for 48 hours (or an appropriate temperature for growth of the test system).

The neutralizer is effective if a=b. The neutralizer is not detrimental to the test system if is b=c.

3. Sterile Letheen Broth 1 ml of Letheen broth was plated for this test.

4. Sterile Phosphate Buffer Dilution Water 1 ml of sterile phosphate buffer was plated for this test.

Results

Modified Time Kill Assay

EQ Ag Fruit & Vegetable Wash—Samples A, B, C, D (C+2% Lactic Acid)

Sample E—Control 150 ppm Chlorine Solution Made Fresh

*Pseudomonas aeruginosa* (ATCC No. 9027)

Sample A (1406-8)

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.00% | 99.00% | 99.840% | 98.947% |
| 60 seconds | 99.60% | 99.530% | 99.50% | 99.543% |
| 5 minutes | 99.920% | 99.940% | 99.90% | 99.920% |
| 10 minutes | 99.990% | 99.990% | 99.90% | 99.960% |
| 15 minutes | 99.990% | 99.990% | 99.990% | 99.990% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.
Modified Time Kill Assay:
  EQ Ag Fruit & Vegetable Wash—Samples A, B, C, D (C+2% Lactic Acid)
    Sample E—Control 150 ppm Chlorine Solution Made Fresh

*Pseudomonas aeruginosa* (ATCC No. 9027)

Sample B (1407-8)

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.500% | 99.580% | 99.550% | 99.543% |
| 60 seconds | 99.990% | 99.980% | 99.960% | 99.977% |
| 5 minutes | 99.990% | 99.990% | 99.990% | 99.990% |
| 10 minutes | 99.990% | 99.990% | 99.990% | 99.990% |
| 15 minutes | 99.990% | 99.990% | 99.990% | 99.990% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.
Modified Time Kill Assay:
  EQ Ag Fruit & Vegetable Wash—Samples A, B, C, D (C+2% Lactic Acid)
    Sample E—Control 150 ppm Chlorine Solution Made Fresh

*Pseudomonas aeruginosa* (ATCC No. 9027)

Sample C (1408-8)

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.550% | 99.480% | 99.530% | 99.520% |
| 60 seconds | 99.750% | 99.760% | 99.790% | 99.767% |
| 5 minutes | 99.990% | 99.990% | 99.990% | 99.990% |
| 10 minutes | 99.990% | 99.990% | 99.990% | 99.990% |
| 15 minutes | 99.990% | 99.990% | 99.990% | 99.990% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.
Modified Time Kill Assay:
  EQ Ag Fruit & Vegetable Wash—Samples A, B, C, D (C+2% Lactic Acid)
    Sample E—Control 150 ppm Chlorine Solution Made Fresh

*Pseudomonas aeruginosa* (ATCC No. 9027)

Sample D (1409-8)-(Sample C+2% Lactic Acid)

Percent Reduction indicated for test time points.
Note: NG=No Growth Detected at 48 hour
  G=Growth Detected at 48 hours.

| Average Initial Bacterial Counts = 30,000,000 cts per 0.2 ml | | | | |
|---|---|---|---|---|
| Time Point | Percent Reduction | | | |
| 30 seconds | 99.70% | 99.620% | 99.570% | 99.630% |
| 60 seconds | 99.80% | 99.850% | 99.750% | 99.800% |
| 5 minutes | 99.880% | 99.880% | 99.860% | 99.873% |
| 10 minutes | 99.990% | 99.990% | 99.990% | 99.990% |
| 15 minutes | 99.990% | 99.990% | 99.990% | 99.990% |
| Positive Controls | G | G | G | G |
| Negative Controls | NG | NG | NG | NG |

Note: Time Kill Value represents the lower value of two (2)separate analytical procedures performed in quadruplicate for the determination of the Bacteriological Kinetics.
Modified Time Kill Assay:
  EQ Ag Fruit & Vegetable Wash—Samples A, B, C, D (C+2% Lactic Acid)
    Sample E—Control 150 ppm Chlorine Solution Made Fresh

*Pseudomonas aeruginosa* (ATCC No. 9027)

Sample E (1410-8)—150 PPM Chlorine Control

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.
Modified Time Kill Assay:
 EQ Ag Fruit & Vegetable Wash—Samples B Original Retain

*Staphylococcus aureus* (ATCC No. 6538)

Sample B Submitted

Percent Reduction indicated for test time points.
Note: NG=No Growth Detected at 48 hours incubation
 G=Growth Detected at 48 hours incubation

| Average Initial Bacterial Counts = 23,000,000 cts per 0.2 ml | | | | |
|---|---|---|---|---|
| Time Point | Percent Reduction | | | Average |
| 30 seconds | 99.9531% | 99.9568% | 99.9623% | 99.9574% |
| 60 seconds | 99.9635% | 99.9542% | 99.9682% | 99.9620% |
| 5 minutes | 99.9697% | 99.8938% | 99.9712% | 99.9449% |
| 10 minutes | 99.9739% | 99.9822% | 99.9711% | 99.9757% |
| 15 minutes | 99.9979% | 99.9881% | 99.9557% | 99.9801% |
| Positive Controls | G | G | G | G |
| Negative Controls | NG | NG | NG | NG |

Note: Kill Time Value represents the lower value of two (2) separate analytical procedures performed in quadruplicate for the determination of the Bacteriological Kinetics.
Modified Time Kill Assay:
 EQ Ag Fruit & Vegetable Wash—Original Sample B

*Pseudomonas aeruginosa* (ATCC No. 9027)

Sample B Submitted

Percent Reduction indicated for test time points.
Note: NG=No Growth Detected at 48 hours incubation
 G=Growth Detected at 48 hours incubation

| Average Initial Bacterial Counts = 23,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.
Modified Time Kill Assay:
 EQ Ag Fruit & Vegetable Wash—Original Sample B

*Salmonella choleraesuis* (ATCC No.14028)

Sample B Submitted

Percent Reduction indicated for test time points.
Note: NG=No Growth Detected at 48 hours incubation
 G=Growth Detected at 48 hours incubation

| Average Initial Bacterial Counts = 23,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.
Modified Time Kill Assay:
 EQ Ag Fruit & Vegetable Wash—K080522 Sample B

*Staphylococcus aureus* (ATCC No. 6538)

Sample B Kappa Labs Produced—K080522

Percent Reduction indicated for test time points.
Note: NG=No Growth Detected at 48 hours incubation
 G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.8989% | 99.8568% | 99.9757% | 99.9104% |
| 60 seconds | 99.9739% | 99.9862% | 99.9749% | 99.9783% |
| 5 minutes | 99.9375% | 99.9529% | 99.9491% | 99.9465% |
| 10 minutes | 99.9677% | 99.9818% | 99.9599% | 99.9698% |
| 15 minutes | 99.9854% | 99.9863% | 99.9734% | 99.9817% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:

EQ Ag Fruit & Vegetable Wash—K080522 Sample B

*Pseudomonas aeruginosa* (ATCC No. 9027)

Sample B Kappa Labs Produced—K080522

Percent Reduction indicated for test time points.
Note: NG=No Growth Detected at 48 hours incubation
G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:

EQ Ag Fruit & Vegetable Wash—K080603-2% Lactic Acid Solution

*Salmonella choleraesuis* (ATCC No. 14028)

Sample B Kappa Labs Produced—K080603

Percent Reduction indicated for test time points.
Note: NG=No Growth Detected at 48 hours incubation
G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:

EQ Ag Fruit & Vegetable Wash—K080603-2% Lactic Acid Solution

*Staphylococcus aureus* (ATCC No. 6538)

Sample B Kappa Labs Produced—K080603

Percent Reduction indicated for test time points.
Note: NG=No Growth Detected at 48 hours incubation
G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.9391% | 99.9523% | 99.9478% | 99.9464% |
| 60 seconds | 99.9802% | 99.9845% | 99.9745% | 99.9797% |
| 5 minutes | 99.9625% | 99.9556% | 99.9699% | 99.9627% |
| 10 minutes | 99.9781% | 99.9888% | 99.9856% | 99.9842% |
| 15 minutes | 99.9870% | 99.9916% | 99.9819% | 99.9868% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:

EQ Ag Fruit & Vegetable Wash—K080603-2% Lactic Acid Solution

*Pseudomonas aeruginosa* (ATCC No. 14028)

Sample B Kappa Labs Produced—K080603

Percent Reduction indicated for test time points.
Note: NG=No Growth Detected at 48 hours incubation
G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:
  EQ Ag Fruit & Vegetable Wash—150 PPM Chlorine Control

*Salmonella choleraesuis* (ATCC No.14028)

Sample B Kappa Labs Produced—K080603

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:
  EQ Ag Fruit & Vegetable Wash—150 PPM Chlorine Control

*Staphylococcus aureus* (ATCC No. 6538)

150 PPM Fresh Control Solution

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:
  EQ Ag Fruit & Vegetable Wash—150 PPM Chlorine Control

*Pseudomonas aeruginosa* (ATCC No. 14028)

150 PPM Fresh Control Solution

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinetics.

Modified Time Kill Assay:
  EQ Ag Fruit & Vegetable Wash—150 PPM Chlorine Control

*Salmonella choleraesuis* (ATCC No.14028)

150 PPM Fresh Control Solution

Percent Reduction indicated for test time points.
Note: NG=No Growth Detected at 48 hours incubation
  G=Growth Detected at 48 hours incubation

| Average Initial Bacterial Counts = 30,000,000 cts per 0.2 ml | | | | |
|---|---|---|---|---|
| Time Point | Percent Reduction | | | |
| 30 seconds | 99.999% | 99.999% | 99.999% | 99.999% |
| 60 seconds | 99.999% | 99.999% | 99.999% | 99.999% |
| 5 minutes | 99.999% | 99.999% | 99.999% | 99.999% |
| 10 minutes | 99.999% | 99.999% | 99.999% | 99.999% |
| 15 minutes | 99.999% | 99.999% | 99.999% | 99.999% |
| Positive Controls | G | G | G | G |
| Negative Controls | NG | NG | NG | NG |

Note: Time Kill Value represents the lower value of two (2) separate analytical procedures performed in quadruplicate for the determination of the Bacteriological Kinectics.

Modified rime Kill Assay: Chemical Summary:
EQ Ag Fruit & Vegetable Wash

Formulation Summary

Kappa Laboratories produced three (3) solutions in order to vary the concentrations of the tested actives.

Sample "A"

Sample "A" has 12% Biosoft Actives—2% More than Normal Blend (Sample "C"=8.83%)

| | |
|---|---|
| Caustic Soda Beads | 1.39% |
| Biosoft S-101 96% Active | 10.83% |
| Niaproof 08 Ethylhexyl Sulfate 39% | 10.00% |

Sample "B"

Sample "B" has 26% Ethyl Hexyl Sulfate Actives—16% More than Normal Blend

| | |
|---|---|
| Caustic Soda Beads | 1.16% |
| Biosoft S-101 96% Active | 8.83% |
| Niaproof 08 Ethylhexyl Sulfate 39% | 26.00% |

Sample "C"

Sample "C" has 10% Ethyl Hexyl Sulfate Actives—Normal Blend

| | |
|---|---|
| Caustic Soda Beads | 1.16% |
| Biosoft S-101 96% Active | 8.83% |
| Niaproof 08 Ethylhexyl Sulfate 39% | 10.00% |

Production Summary 500 ml of Solution # K080522B

Step #1: Weigh NaOH and transfer into a 600 ml glass beaker. Add 100 ml of water and mix to dissolve. Temperature rose to 36°-37° C. in 2 minutes.

Step #2: Add Biosoft (viscous) steadily with constant stirring. The temperature increases (Exothermic reaction) to 47° C. solution is cloudy but with the mixing begins to blend to a clear yellow/amber solution. Rinse beaker with water and pour into solution.

Step #3: Add Niaproof 08—the Niaproof 08 is less viscous and appears to blend well in original solution.

Discussion

The EQ Ag Fruit & Vegetable Wash was consistently effective in exerting On-Contact Bacteriocidal Activity at >99.99% level of kill at time exposures of as early as about 30 seconds with consistent results when assayed up to about 15 minutes.

Example 4

Modified Time Kill Study Assay: EQ Ag Formula "B"
Culture Media:
Nutrient Broth (BBL) was prepared according to manufacturer's directions (see above). 10 ml quantities were dispensed into 20×150 mm test tubes, capped, and autoclaved for 20 minutes at 121° C.
Nutrient Agar (BBL) was prepare according to manufacturer's directions (see above). 10 ml quantities were dispensed into 20×150 mm test tubes, capped and autoclaved for 20 minutes at 121° C. Slanted until cooled and solidified.
Subculture Media:
Tryptone Glucose Extract Agar (BBL) was prepared according to manufacturer's directions. Dispense in quantities suitable for easy handling and aseptic technique. Autoclaved for 20 minutes at 121° C.
FCD Broth (BBL) was prepared as discussed above. Dispensed in 99 ml quantities into milk dilution bottles or 9 mls into 25×150 ml test tubes (modified procedure). Autoclaved for 20 minutes at 121° C.
Reagents and Apparatus
Phenol Coefficient Method, AOC 14: Chapter 4, pg. 65.
1. Phenol Stock Solution (5% W/V)
2. Phosphate Buffer Stock (0.25 m)
34.0 g $KH_2PO_4$ was dissolved in 500 ml of Milli-Q water and adjusted to pH 7.2 with IN NaOH and diluted to 1 L.
3. Phosphate Buffer Dilution Water
1.25 ml of 0.25M phosphate buffer stock was added to 1L of Milli-Q water and mixed. Dispensed in 99 ml portions in milk dilution bottles. Autoclaved for 20 minutes at 121° C.
4. Glassware
50 ml beakers with magnetic stir bars were covered with aluminum foil and sterilized for 20 minutes at 121° C. For modified study, sterile disposable 50 ml centrifuge tubes (Baxter Cat. No. C3920-50A or equivalent) were used.
5. Petri Dishes
Sterile disposable petri dishes 15×100 mm.
6. Pipettes
Sterile disposable pipettes.
7. Transfer Loops
Transfer loops held in a suitable holder with a 4 mm diameter of Platinum-rhodium, 1 inch long and bent at a 30-degree angle and used, for example, in volume transfer during testing. Suitable metal or plastic disposable transfer loops were used, for example, during daily culture transfer.
8. Magnetic Stir Plate
9. Vortex Mixer (modified procedure)
Test Systems
*Salmonella typhimurium* (ATCC No. (14028))
*Staphylococcus aureus* (ATCC No. (6538)
Maintained on nutrient agar slants by monthly transfers. Slants stored at 4° C. From the stock culture a tube of nutrient broth was inoculated and at least 3 consecutive 24 hour transfers in nutrient broth incubated at 37°±2° C. before using culture for testing. (If only one daily transfer has been missed, it is not necessary to repeat the 3 consecutive transfers). 22-26 hour broth culture of organisms grown in nutrient broth at 37° C.±2° C. were vortexed and allowed to settle for 15 minutes prior to testing.
Controls
Negative controls for all medias were performed by incubation of uninoculated media. Positive controls were performed for all organisms by plating directly onto the appropriate media employed for the assay. Broths were tested for positive growth inoculation with appropriate organism.

Operating Technique—Time Kill Study
1. 10 ml of antibacterial test product was placed in 50 ml beaker and placed on a magnetic stir plate. Speed of mixer was adjusted for rapid mixing without creating air bubbles.
2. 0.2 ml of test organism was added to antibacterial test product.
3. After each desired exposed time (such as 15, 30 or 60 seconds), 1.0 ml of inoculated antibacterial test product was removed and subcultured into 99 ml of FCD Broth. This represents a 10 to the −2 dilution. Subcultured again from first bottle of FCD Broth to second bottle of FCD Broth. This represents a 10 to the −4 dilution.
4. Enumerated by serial dilutions and pour plate technique. (For antibacterial test product, 10 to the −2, 10 to the −3, 10 to the −4 were plated in duplicate.)
5. For each test organism tested, initial test organism numbers were determined. This was accomplished by replacing 10 ml of antibacterial soap with 10 ml phosphate buffer and repeating steps 1-4 with the exception of exposure time. (Plate 10 to the −5, 10 to the −6 in triplicate for # control.)

Operating Technique—Modified Time Kill Study 10 ml of the test substance was placed into a 50 ml centrifuge tube. The test substance in the tube was allowed to equilibrate to test temperature for 40 minutes. 0.2 ml of a 24-hour broth culture was added to 10 ml of the test substance and vortexed vigorously for 10 seconds. Fifteen seconds after adding the suspension, 1 ml of the test substance/culture suspension mixture was removed with a 1 ml syringe and transferred to 9 ml of neutralizer (a 10 to the −1 dilution). The same procedure was repeated for the 30-second exposure. 1 ml from the initial neutralizer (a 10 to the −2 dilution) was transferred. Both 10 to the −2 and 10 to the −3 dilutions from the second neutralizer tube were plated by adding 1 ml and 0.1 ml respectively to separate petri plates. 1 ml of the 10 to the −2 was diluted into 99 ml of phosphate buffered dilution water (PBDW) to result in a 10 to the −4 dilution. 1 ml of the 10 to the −4 dilution was added to a petri plate. The pour plate technique was used with the subculture medium for enumeration of survivors. Inoculum numbers were enumerated by adding 0.2 ml of the 24-hour broth culture to 10 ml of PBDW, vortexed, and then serially diluting in PBDW. Enumeration was also carried out using pour plate technique 10 to the −5 and 10 to the −6 dilutions. All plates were incubated for 48 hours at 37° C.±2° C.

Calculation

I=Initial Bacterial Suspension Count
S=Survivors (Test Substance) Count $\% R = I - s/I \times 100$ Results were reported as a % reduction in relationship to exposure time.

Controls

1. Phenol Resistance Method

From the 5% phenol stock solution, make the appropriate dilutions for the culture to be tested. Test tubes containing 5 ml of each dilution to be tested were placed in a 20° C. water bath for 10 minutes. 0.5 ml of test culture was added to the first dilution of phenol and 30 seconds later the second dilution was seeded and so on until 4.5 minutes have passed. After adding the culture, he tubes were gently agitate to distribute the bacteria. Five minutes after seeding the first test tube, one loop full of phenol culture mixture was transferred to a subculture tube. This procedure was repeated until all tubes have been transferred after 5, 10 and 15 minutes exposure. The subculture tubes were transferred at 37° C.±2° C. for 48 hours.

2. Neutralization Method

Procedures performed in duplicate.

For the Time Kill Study:

The following solutions were inoculated with 0.1 ml of a 10 to the −3 dilution of the test system.

a. 99 ml neutralizer+1 ml test substance use-solution
b. 99 ml neutralizer+1 ml test substance dilution
c. 100 ml phosphate Buffer Dilution Water After a 10 minute contact time, the bacteria were enumerated using serial dilutions and pour plate technique. The plates were incubated at 37° C. for 48 hours (or at an appropriate temperature for growth of the test system).

For the Modified Time Kill Study:

The following solutions were inoculated with 0.1 ml of a 10 to the −3 dilution of the test system.

a. 9 ml neutralizer+1 ml test substance use-solution
b. 9 ml neutralizer+1 ml test substance dilution
c. 10 ml phosphate Buffer Dilution Water After a 10 minute contact time, the bacteria were enumerated using serial dilutions and pour plate technique. The plates were incubated at 37° C. for 48 hours (or at an appropriate temperature for growth of the test system). The neutralizer is effective if a=b. The neutralizer is not detrimental to the test system if b=c.

3. Sterile FCD Broth 1 ml of FCD broth was plated for this test.

4. Sterile Phosphate Buffer Dilution Water 1 ml of sterile phosphate buffer was plated for this test.

Results

TEST Product—EQ Ag Formula "B" Diluted 1:200 Water
*Salmonella typhimurium* (ATCC No. (14028)

Sample Data Results

Percent Reduction indicated for test time points.

Note: NG=No Growth Detected at 48 hours incubation
G=Growth Detected at 48 hours incubation

| Average Initial Bacterial Counts = $63.6 \times 10^7$ cts per 0.2 ml | | | |
|---|---|---|---|
| Time Point | Initial Population | Average Survival (CFU) | Average Percent Reduction |
| 30 seconds | $63.6 \times 10^7$ | $38.0 \times 10^4$ | 99.94% |
| 1 minute | $63.6 \times 10^7$ | $31.0 \times 10^4$ | 99.95% |
| 5 minutes | $63.6 \times 10^7$ | $31.5 \times 10^4$ | 99.95% |
| 10 minutes | $63.6 \times 10^7$ | $31.0 \times 10^4$ | 99.95% |
| 15 minutes | $63.6 \times 10^7$ | $35.0 \times 10^4$ | 99.94% |
| Positive Controls | G | G | G |
| Negative Controls | NG | NG | NG |

Note: Time Kill Value represents procedures performed in quadruplicate for the determination of the Bacteriologica Kinetics.

TEST Product—EQ Ag Formula "B" Diluted 1:400 Water

*Salmonella typimurium* (ATCC No. (14028))

Sample Data Results

Percent Reduction indicated for test time points.
Note: NG=No Growth Detected at 48 hours incubation
G=Growth Detected at 48 hours incubation

| Time Point | Initial Population | Average Survival (CFU) | Average Percent Reduction |
|---|---|---|---|
| Average Initial Bacterial Counts = $63.6 \times 10^7$ cts per 0.2 ml | | | |
| 30 seconds | $63.6 \times 10^7$ | $71.5 \times 10^4$ | 99.89% |
| 1 minute | $63.6 \times 10^7$ | $65.0 \times 10^4$ | 99.90% |
| 5 minutes | $63.6 \times 10^7$ | $49.0 \times 10^4$ | 99.92% |
| 10 minutes | $63.6 \times 10^7$ | $33.5 \times 10^4$ | 99.95% |
| 15 minutes | $63.6 \times 10^7$ | $35.0 \times 10^4$ | 99.94% |
| Positive Controls | G | G | G |
| Negative Controls | NG | NG | NG |

Note: Time Kill Value represents procedures performed in quadruplicate for the determination of the Bacteriological Kinetics.

TEST Product—EQ Ag Formula "B" Diluted 1:200 Water+50 PPM Free Chlorine

*Salmonella typhimurium* (ATCC No. (14028)).

Sample Data Results

Percent Reduction indicated for test time points.
Note: NG=No Growth Detected at 48 hours incubation
G=Growth Detected at 48 hours incubation

| Time Point | Initial Population | Average Survival (CFU) | Average Percent (Reduction) |
|---|---|---|---|
| Average Initial Bacterial Counts = $62.1 \times 10^7$ cts per 0.2 ml | | | |
| 30 seconds | $62.1 \times 10^7$ | 1.0 | 99.999% |
| 1 minute | $62.1 \times 10^7$ | 1.0 | 99.999% |
| 5 minutes | $62.1 \times 10^7$ | 1.0 | 99.999% |
| 10 minutes | $62.1 \times 10^7$ | 1.0 | 99.999% |
| 15 minutes | $62.1 \times 10^7$ | 1.0 | 99.999% |
| Positive Controls | G | G | G |
| Negative Controls | NG | NG | NG |

Note: Time Kill Value represents procedures performed in quadruplicate for the determination of the Bacteriological Kinetics.

TEST Product—EQ Ag Formula "B" Diluted 1:600 Water

*Salmonella typhimurium* (ATCC No. (14028))

Sample Data Results

Percent Reduction indicated for test time points.
Note: NG=No Growth Detected at 48 hours incubation
G=Growth Detected at 48 hours incubation

| Time Point | Initial Population | Average Survival (CFU) | Average Percent (Reduction) |
|---|---|---|---|
| Average Initial Bacterial Counts = $90.5 \times 10^7$ cts per 0.2 ml | | | |
| 30 seconds | $90.5 \times 10^7$ | $665.0 \times 10^3$ | 99.93% |
| 1 minute | $90.5 \times 10^7$ | $498.5 \times 10^3$ | 99.95% |
| 5 minutes | $90.5 \times 10^7$ | $498.0 \times 10^3$ | 99.95% |
| 10 minutes | $90.5 \times 10^7$ | $438.5 \times 10^3$ | 99.96% |
| 15 minutes | $90.5 \times 10^7$ | $413.0 \times 10^3$ | 99.96% |
| Positive Controls | G | G | G |
| Negative Controls | NG | NG | NG |

Note: Time Kill Value represents procedures performed in quadruplicate for the determination of the Bacteriological Kinetics.

TEST Product—EQ Ag Formula "B" Diluted 1:600 Water

*Staphylococcus aureus* (ATCC No. (6538))

Sample Data Results

Percent Reduction indicated for test time points.
Note: NG=No Growth Detected at 48 hours incubation
G=Growth Detected at 48 hours incubation

| Time Point | Initial Population | Average Survival (CFU) | Average Percent (Reduction) |
|---|---|---|---|
| Average Initial Bacterial Counts = $67.7 \times 10^7$ cts per 0.2 ml | | | |
| 30 seconds | $67.7 \times 10^7$ | $346.0 \times 10^3$ | 99.95% |
| 1 minute | $67.7 \times 10^7$ | $346.0 \times 10^3$ | 99.95% |
| 5 minutes | $67.7 \times 10^7$ | $308.0 \times 10^3$ | 99.95% |
| 10 minutes | $67.7 \times 10^7$ | $258.0 \times 10^3$ | 99.96% |
| 15 minutes | $67.7 \times 10^7$ | $237.0 \times 10^3$ | 99.96% |
| Positive Controls | G | G | G |
| Negative Controls | NG | NG | NG |

Note: Time Kill Value represents procedures performed in quadruplicate for the determination of the Bacteriological Kinetics.

Test Product—EQ Ag Formula "B" Diluted 1:600
Water+25 PPM Free Chlorine

*Salmonella typhimurium* (ATCC No. (14028))

Sample Data Results

Percent Reduction indicated for test time points.
Note: NG=No Growth Detected at 48 hours incubated
G=Growth Detected at 48 hours incubated Average Initial Bacterial Counts = $7.52 \times 10^6$ cts per 0.2 ml

| Time Point | Initial Population | Average Survival (CFU) | Average Percent (Reduction) |
|---|---|---|---|
| 30 seconds | $7.52 \times 10^6$ | $1.90 \times 10^3$ | 99.98% |
| 1 minute | $7.52 \times 10^6$ | $1.85 \times 10^3$ | 99.98% |
| 5 minutes | $7.52 \times 10^6$ | $1.20 \times 10^3$ | 99.99% |
| 10 minutes | $7.52 \times 10^6$ | 0 | 99.99% |
| 15 minutes | $7.52 \times 10^6$ | 0 | 99.99% |
| Positive Controls | G | G | G |
| Negative Controls | NG | NG | NG |

Note: Time Kill Value represents procedures performed in quadruplicate for the determination of the Bacteriological Kinetics.

Test Product—EQ Ag Formula "B" Diluted 1:400
Water+2% Lactic Acid

*Salmonella typhimurium* (ATCC No. (14028))

Sample Data Results

Percent Reduction indicated for test time points.
Note: NG=No Growth Detected at 48 hours incubation
G=Growth Detected at 48 hours incubation Average Initial Bacterial Counts = $7.57 \times 10^6$ cts per 0.2 ml

| Time Point | Initial Population | Average Survival (CFU) | Average Percent (Reduction) |
|---|---|---|---|
| 30 seconds | $7.57 \times 10^6$ | $6.00 \times 10^2$ | 99.99% |
| 1 minute | $7.57 \times 10^6$ | 0 | 99.99% |
| 5 minutes | $7.57 \times 10^6$ | 0 | 99.99% |
| 10 minutes | $7.57 \times 10^6$ | 0 | 99.99% |
| 15 minutes | $7.57 \times 10^6$ | 0 | 99.99% |
| Positive Controls | G | G | G |
| Negative Controls | NG | NG | NG |

Note: Time Kill Value represents procedures performed in quadruplicate for the determination of the Bacteriological Kinetics.

Discussion

The EQ Ag Formula "B" Product is consistently effective in exerting greater than a three (3) log bacterial reduction when tested against *Salmonella typhimurium*. The EQ Ag Formula B exhibited a greater than three (3) log reduction when assayed against *Staphylococcus aureus*. The EQ Ag Formula "B" Product is effective in concentrations of 1:200 through a dilution range of 1:600 in having a continued effectiveness in exerting On-Contact Bactericidal Activity against *Salmonella typhimurium*. The reductions were consistent with a "plateau" like kinetics as related to EQ Ag Formula B Product concentration.

The bactericidal properties of the EQ Ag Formula "B" Product is significantly potentiated in the presence of low levels of Chlorine, 50 ppm, in effectively exerting greater than a five (5) log bacterial reduction when tested against *Salmonella typhimurium*. Note, bactericidal activity in the complete reduction of the *Salmonella typhimurium* bacterial inoculum was as early as 30 seconds.

In conclusion, the dilutions in Example 4 demonstrate the superiority and surprising and unexpected results of formula B over the commercial blend tested in the study completed at full strength in Example 3.

What is claimed is:

1. A method of killing or inhibiting a microorganism or a pathogen, the method comprising contacting the microorganism or the pathogen with an effective amount of a composition comprising:
   (a) ethylhexyl sulfate of the formula

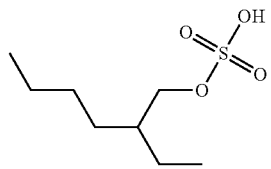

or a salt thereof; and
   (b) an alkylbenzenesulfonic acid of the formula

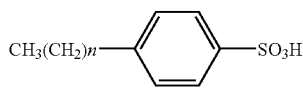

or a salt thereof, wherein n is about 5 to about 20; and
   (c) a carrier comprising water;
   wherein the ethylhexyl sulfate, or salt thereof, and the alkylbenzenesulfonic acid, or salt thereof, are present in a weight ratio such that based upon a weight basis, the amount of ethylhexyl sulfate, or salt thereof, is at least 100% that of the alkylbenzenesulfonic acid, or salt thereof, and is no more than 300% of the alkylbenzenesulfonic acid, or salt thereof;
   wherein the composition further comprises at least one of sodium hydroxide and potassium hydroxide such that the pH of the composition contacting the microorganism or pathogen is above about 6;
   wherein the composition does not comprise chlorine dioxide;
   for a period of time effective to kill or inhibit the microorganism or the pathogen.

2. The method of claim 1, wherein n has an average value of about 9 to about 11.

3. The method of claim 1, wherein the sodium hydroxide, potassium hydroxide, or combination thereof is present in ratio of less than about 1:4, relative to the ethylhexyl sulfate, or salt thereof.

4. The method of claim 1, wherein the composition comprises:
   (a) about 13 wt.% ethylhexyl sulfate, or salt thereof;
   (b) about 11 wt.% dodecylbenzenesulfonic acid, or salt thereof;
   (c) about 1.4 wt.% sodium hydroxide, and
   (d) water.

5. The method of claim 1, wherein the contacting is in vitro.

6. The method of claim 1, wherein the contacting is in vivo.

7. The method of claim 1, wherein the contacting occurs on a surface of a plant or on a topical surface of a mammal.

8. The method of claim 1, wherein the microorganism or the pathogen is at least one of a bacteria, a virus, a fungus, a mold and a mildew.

9. The method of claim 1, wherein the microorganism or pathogen is at least one of a gram-negative bacteria, gram-positive bacteria and an enteric bacteria.

10. The method of claim 1, wherein the period of time effective to kill or inhibit the microorganism or the pathogen is less than about 30 seconds.

11. The method of claim 7, wherein the mammal is afflicted, or a risk thereof, with at least one of a bacterial disease, viral disease and a fungal disease.

12. The method of claim 7, wherein the plant is afflicted, or at risk thereof, with at least one of a bacterial disease and a fungal disease.

13. The method of claim 1, wherein n has an average value of about 8 to about 12.

14. The method of claim 1, wherein the composition is formulated as a fluid liquid.

15. The method of claim 1, wherein the composition is formulated for application by spraying the composition.

16. The method of claim 1, wherein the composition is formulated for application by spraying the composition.

17. The method of claim 1, wherein the composition optionally comprises a disinfectant selected from the group consisting of chlorine gas ($Cl_2$), ozone ($O_3$), lactic acid, ultraviolet light, peroxides, peracetic acid, potassium sorbate, lactic acid, and combinations thereof.

18. A method of washing a plant, the method comprising contacting the plant with an effective amount of a composition comprising:

(a) ethylhexyl sulfate of the formula

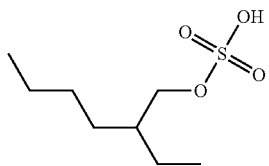

or a salt thereof; and
(b) an alkylbenzenesulfonic acid of the formula

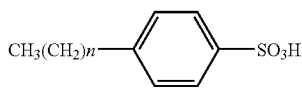

or a salt thereof, wherein n is about 5 to about 20; and (c) a carrier comprising water;

wherein the ethylhexyl sulfate, or salt thereof, and the alkylbenzenesulfonic acid, or salt thereof, are present in a weight ratio such that based upon a weight basis, the amount of ethylhexyl sulfate, or salt thereof, is at least 100% that of the alkylbenzenesulfonic acid, or salt thereof, and is no more than 300% of the alkylbenzenesulfonic acid, or salt thereof;

wherein the composition further comprises at least one of sodium hydroxide and potassium hydroxide such that the pH of the composition contacting the microorganism or pathogen is above about 6;

wherein the composition does not comprise chlorine dioxide;

for a period of time effective to wash the plant.

19. The method of claim 18, wherein n has an average value of about 9 to about 11.

20. The method of claim 18, wherein the sodium hydroxide, potassium hydroxide, or combination thereof is present in ratio of less than about 1:4, relative to the ethylhexyl sulfate, or salt thereof.

21. The method of claim 18, wherein the composition comprises:

(a) about 13 wt.% ethylhexyl sulfate, or salt thereof;
(b) about 11 wt.% dodecylbenzenesulfonic acid, or salt thereof;
(c) about 1.4 wt.% sodium hydroxide, and
(d) water.

22. The method of claim 18, wherein an edible part of the plant is washed.

23. The method of claim 18, wherein the plant is washed before harvesting.

24. The method of claim 18, wherein the plant is washed after harvesting.

25. The method of claim 18, wherein the period of time effective to wash the plant is less than about 30 seconds.

26. The method of claim 18, wherein n has an average value of about 8 to about 12.

27. The method of claim 18, wherein the composition is formulated as a fluid liquid.

28. The method of claim 18, wherein the composition optionally comprises a disinfectant selected from the group consisting of chlorine gas ($Cl_2$), ozone ($O_3$), lactic acid, ultraviolet light, peroxides, peracetic acid, potassium sorbate, lactic acid, and combinations thereof.

* * * * *

UNITED STATES PATENT AND TRADEMARK OFFICE
CERTIFICATE OF CORRECTION

PATENT NO.        : 8,911,755 B2
APPLICATION NO.   : 12/489362
DATED             : December 16, 2014
INVENTOR(S)       : Curry et al.

Page 1 of 1

It is certified that error appears in the above-identified patent and that said Letters Patent is hereby corrected as shown below:

On the title page, in column 2, under "Other Publications", line 33, after "pgs.", insert --"¶Colombian Application Serial No. 11-177132, Office Action mailed 09-24-14", 18 pgs.
SAPERS, et al., "Antimicrobial treatments for minimally processed cantaloupe melon", (2001).--, therefor In the Claims In column 48, line 43, in Claim 28, delete "($Cl_2$)" and insert --($Cl_2$)--, therefor Signed and Sealed this
Twenty-eighth Day of July, 2015

Michelle K. Lee
*Director of the United States Patent and Trademark Office*